(12) United States Patent
Björnson et al.

(10) Patent No.: US 6,827,906 B1
(45) Date of Patent: Dec. 7, 2004

(54) CONTINUOUS FORM MICROSTRUCTURE ASSAY ARRAY

(75) Inventors: Torleif Ove Björnson, Gilroy, CA (US); Laurence R. Shea, San Jose, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 0 days.

(21) Appl. No.: 09/568,456

(22) Filed: May 9, 2000

Related U.S. Application Data

(63) Continuation of application No. 08/950,403, filed on Oct. 15, 1997, now abandoned.

(51) Int. Cl.[7] .............................. G01N 31/20; B01L 3/00
(52) U.S. Cl. .......................... 422/101; 422/58; 422/66; 422/82.01; 422/102; 204/601; 204/603
(58) Field of Search ........................... 436/44; 422/101, 422/66, 102, 82.01, 82.02, 100, 58; 204/601, 603

(56) References Cited

U.S. PATENT DOCUMENTS

| | | | |
|---|---|---|---|
| 4,271,139 A | 6/1981 | Hart ............................... 424/1 |
| 4,273,639 A | 6/1981 | Gottermeier ............ 204/195 R |
| 4,382,074 A | 5/1983 | Hart ............................ 436/537 |
| 4,420,502 A | 12/1983 | Conley ..................... 425/54.1 |
| 4,521,445 A | 6/1985 | Nablo et al. ................... 427/44 |
| 4,626,462 A | 12/1986 | Kober et al. ................. 428/137 |
| 4,675,786 A | 6/1987 | Mizuko et al. ............. 361/398 |
| 4,715,928 A | 12/1987 | Hamby ....................... 156/620 |
| 4,812,213 A | 3/1989 | Barton et al. ................. 204/15 |
| 4,908,112 A | 3/1990 | Pace ........................... 204/299 |
| 4,913,858 A | 4/1990 | Miekka et al. ............... 264/1.3 |
| 4,952,266 A | 8/1990 | Tsuruta et al. ............... 156/243 |
| 4,965,049 A | 10/1990 | Lillig et al. ................. 422/68.1 |
| 5,030,418 A | 7/1991 | Miyata ......................... 422/63 |
| 5,104,621 A | 4/1992 | Pfost et al. .................... 422/67 |
| 5,126,022 A | 6/1992 | Soane et al. ............. 204/180.1 |
| 5,132,012 A | 7/1992 | Miura et al. ............. 210/198.2 |
| 5,180,480 A | 1/1993 | Manz ......................... 204/299 |
| 5,202,231 A | 4/1993 | Drmanac et al. .............. 435/6 |
| 5,219,640 A | 6/1993 | Grazit et al. ................. 428/209 |
| 5,250,263 A | 10/1993 | Manz ........................... 422/81 |
| 5,252,743 A | 10/1993 | Barrett et al. ............... 548/303 |
| 5,296,114 A | 3/1994 | Manz ......................... 204/180 |
| 5,356,525 A | 10/1994 | Goodale et al. ............ 204/299 |
| 5,376,252 A | 12/1994 | Ekstrom et al. ............ 204/299 |
| 5,411,858 A | 5/1995 | McGeehan et al. ............ 435/4 |
| 5,455,008 A | 10/1995 | Earley et al. ............... 422/100 |
| 5,500,071 A | 3/1996 | Kaltenbach et al. ........ 156/272 |

(List continued on next page.)

FOREIGN PATENT DOCUMENTS

| WO | WO 94/29400 | 12/1994 |
|---|---|---|
| WO | AO 97/01755 | 1/1997 |

OTHER PUBLICATIONS

Barron, et al., *Separation and Purification Methods* (1995), 24(1):1–118.

(List continued on next page.)

*Primary Examiner*—Jan M. Ludlow
(74) *Attorney, Agent, or Firm*—Stephen C. Macevicz

(57) ABSTRACT

A continuous form microstructure array device is constructed as a flexible elongate film laminate containing a plurality of microstructures or arrays of microstructures arranged serially lengthwise along the laminate. The laminate can be continuously drawn from a supply roll or stack, advanced within an analytic device and, when analysis is complete, taken up in a storage roll or stack. The device provides for high throughput microfluidic processing.

4 Claims, 11 Drawing Sheets

U.S. PATENT DOCUMENTS

| | | |
|---|---|---|
| 5,521,030 A | 5/1996 | McGrew .......................... 430/1 |
| 5,544,008 A | 8/1996 | Dimmick et al. ............ 361/684 |
| 5,585,277 A | 12/1996 | Bowie et al. ................ 436/518 |
| 5,589,330 A | 12/1996 | Shuber ........................... 435/5 |
| 5,595,712 A | 1/1997 | Harbster et al. ............. 422/129 |
| 5,599,695 A | 2/1997 | Pease et al. ................ 435/91.1 |
| 5,615,088 A | 3/1997 | Mizumo ...................... 361/749 |
| 5,631,734 A | 5/1997 | Stern et al. ................. 356/317 |
| 5,637,509 A | 6/1997 | Hemmila et al. ............ 436/537 |
| 5,658,413 A | 8/1997 | Kaltenbach et al. |
| 5,792,943 A | 8/1998 | Craig |
| 5,880,071 A | 3/1999 | Parce et al. |
| 5,885,470 A | 3/1999 | Parce et al. .................... 216/33 |
| 6,235,471 B1 * | 5/2001 | Knapp et al. ................... 435/6 |
| 6,375,871 B1 | 4/2002 | Bentsen et al. .............. 264/1.6 |
| 6,451,191 B1 | 9/2002 | Bentsen et al. ............. 204/600 |
| 2002/0098124 A1 | 7/2002 | Bentsen et al. ............. 422/100 |

OTHER PUBLICATIONS

Effenhauser, et al., *Anal. Chem.* (1994), 66:2949–53.
Harrison, et al., *Science* (1993), 261:895–7.
Jacobson, et al., *Anal. Chem.* (1994), 66:4217–32.
Stearns, "Flexible Printed Circuitry," 1–289.
Woolley, et al., *PNAS* (1994), 91: 111348–52.

* cited by examiner

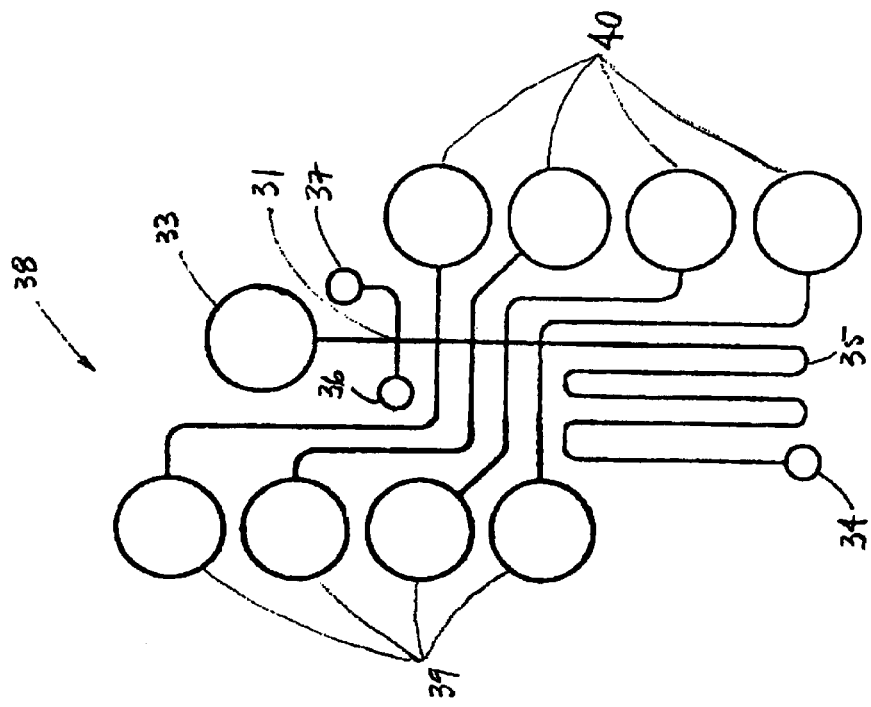
Fig. 3C
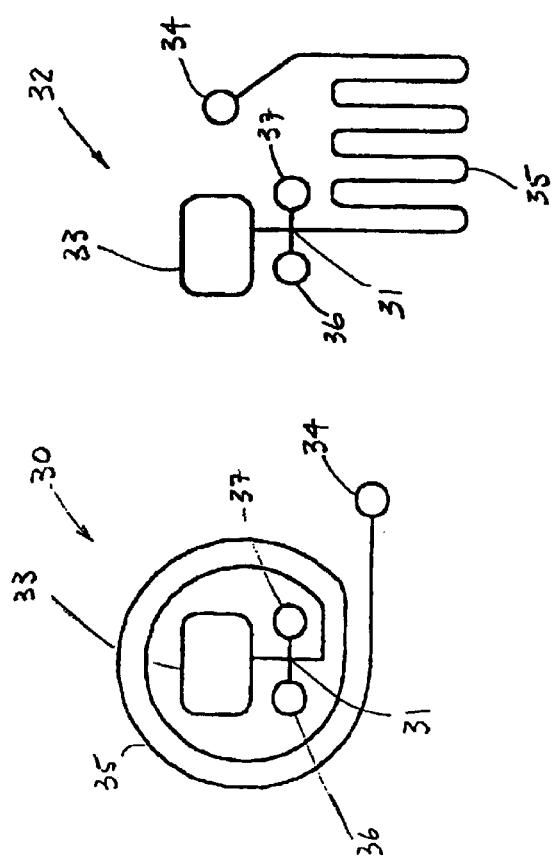
Fig. 3B
Fig. 3A

CONTINUOUS FORM MICROSTRUCTURE ASSAY ARRAY

This application is a continuation of U.S. patent application Ser. No. 08/950,403, filed Oct. 15, 1997, now abandoned.

BACKGROUND

This invention relates to methods and apparatus for high throughput sample analysis.

In a range of technology-based industries, including the chemical, bioscience, biomedical, and pharmaceutical industries, it has become increasingly desirable to develop capabilities for rapidly and reliably carrying out chemical and biochemical reactions in large numbers using small quantities of samples and reagents. Carrying out a massive screening program manually, for example, can be exceedingly time consuming and may be entirely impracticable where only a very small quantity of an important sample or component of interest is available, or where a component of a synthesis or analysis is very costly.

Developments in a variety of fields have resulted in an enormous increase in the numbers of targets and compounds that can be subjected to screening.

Rapid and widespread advances in the scientific understanding of critical cellular processes, for example, has led to rationally designed approaches in drug discovery. Molecular genetics and recombinant DNA technologies have made possible the isolation of many genes, and the proteins encoded by some of these show promise as targets for new drugs. Once a target is identified and the gene is cloned, the recombinant protein can be produced in a suitable expression system. Often receptors and enzymes exist in alternative forms, subtypes or isoforms, and using a cloned target focuses the primary screen on the subtype appropriate for the disease. Agonists or antagonists can be identified and their selectivity can then be tested against the other known subtypes. The availability of such cloned genes and corresponding expression systems require screening methods that are specific, sensitive, and capable of automated very high throughput.

Similarly, an emergence of methods for highly parallel chemical synthesis has increased the need for high throughput screening ("HTS"). Conventionally, preparation of synthetic analogs to the prototypic lead compound was the established method for drug discovery. Natural products were usually isolated from soil microbes and cultured under a wide variety of conditions. The spectrum of organisms employed by the pharmaceutical industry for isolation of natural products has now expanded from actinomycetes and fungi to include plants, marine organisms, and insects. More recently, the chemistry of creating combinatorial libraries has vastly increased the number of synthetic compounds available for testing. Thousands to tens or hundreds of thousands of small molecules can be rapidly and economically synthesized. See, e.g., U.S. Pat. No. 5,252,743 for a discussion of combinatorial chemistry. Thus, combinatorial libraries complement the large numbers of synthetic compounds available from the more traditional drug discovery programs based, in part, on identifying lead compounds through natural product screening.

Accordingly, considerable resources have been directed to developing methods for high-throughput chemical syntheses, screening, and analyses. A considerable art has emerged, in part from such efforts.

Competitive binding assays, originally developed for immunodiagnostic applications, continue to be commonly employed for quantitatively characterizing receptor-ligand interactions. Despite advances in the development of spectrophotometric- and fluorometric-based bioanalytical assays, radiolabeled ligands are still commonly employed in pharmaceutical HTS applications. Although non-isotopic markers promise to be environmentally cleaner, safer, less expensive, and generally easier to use than radioactive compounds, sensitivity limitations have prevented these new methods from becoming widespread. Another major disadvantage of the competition assay is the number of steps, most notably washing steps, required to run assays.

Scintillation proximity assays, discussed for example in U.S. Pat. No. 4,271,139 and U.S. Pat. No. 4,382,074, were developed as a means of circumventing the wash steps required in the above heterogeneous assays. The homogeneous assay technology, which requires no separation of bound from free ligand, is based on the coating of scintillant beads with an acceptor molecule such as, for example, the target receptor.

In another approach to avoiding the use of radioactive labels, especially useful in high-throughput assays, lanthanide chelates are used in time-resolved fluorometry. See, e.g., U.S. Pat. No. 5,637,509.

Automated laboratory workstations have contributed significantly to advances in pharmaceutical drug discovery and genomic science. See, e.g., U.S. Pat. No. 5,104,621 and U.S. Pat. No. 5,356,525, Particularly, robotics technology has played a major role in providing practical means for carrying out HTS methods. See, e.g., U.S. Pat. No. 4,965,049.

Robotic-based high-throughput tools are now routinely used for screening libraries of compounds for the purpose of identifying lead molecules for their therapeutic potential. For example, a screening method for characterizing ligand binding to a given target employing a variety of separation techniques is described in WO 97/01755, and a related method is described in U.S. Pat. No. 5,585,277.

Highly parallel and automated methods for DNA synthesis and sequencing have also contributed significantly to the success of the human genome project, and a competitive industry has developed. Examples of automated DNA analysis and synthesis include, e.g., U.S. Pat. No. 5,455,008; U.S. Pat. No. 5,589,330; U.S. Pat. No. 5,599,695; U.S. Pat. No. 5,631,734; and U.S. Pat. No. 5,202,231.

Computerized data handling and analysis systems have also emerged with the commercial availability of high-throughput instrumentation for numerous life sciences research and development applications. Commercial software, including database and data management software, has become routine in order to efficiently handle the large amount of data being generated.

With the developments outlined above in molecular and cellular biology, combined with advancements in combinatorial chemistry, there has been a huge increase in the number of targets and compounds available for screening. In addition, many new human genes and their expressed proteins are being identified by the human genome project and will therefore greatly expand the pool of new targets for drug discovery. A great need exists for the development of more efficient ultrahigh throughput methods and instrumentation for pharmaceutical and genomic science screening applications.

Miniaturization of chemical analysis systems, employing semiconductor processing methods, including photolithography and other wafer fabrication techniques borrowed from the microelectronics industry, has attracted increasing attention and has progressed rapidly. The so-called "lab-on-a- chip" technology enables sample preparation and analysis to be carried out on-board microfluidic-based cassettes. Moving fluids through a network of interconnecting enclosed microchannels of capillary dimensions is possible using electrokinetic transport methods.

Applications of microfluidics technology embodied in the form of analytical devices has many attractive features for pharmaceutical high throughput screening. Advantages of miniaturization include greatly increased throughput and reduced costs, in addition to low consumption of both samples and reagents and system portability. Implementation of these developments in microfluidics and laboratory automation hold great promise for contributing to advancements in life sciences research and development.

Of particular interest are microfluidics devices in which very small volumes of fluids are manipulated in microstructures, including microcavities and microchannels of capillary dimension, at least in part by application of electrical fields to induce I electrokinetic flow of materials within the microstructures. Application of an electric potential between electrodes contacting liquid media contained within a microchannel having cross-sectional dimensions in the range from about 1 μm to upwards of about 1 mm results in movement of the contents within the channel by electroosmotic flow and/or by electrophoresis. Electrophoresis is movement of electrically charged particles, aggregates, molecules or ions in the liquid medium toward or away from the electrodes. Electroosmotic flow is bulk fluid flow, including movement of the liquid medium and of dissolved or suspended materials in the liquid medium. The extent of bulk fluid flow resulting from application of a given electrical field depends among other factors upon the viscosity of the medium and on the electrical charge on the wall of the microchannel. Both electroosmotic flow and electrophoresis can be used to transport substances from one point to another within microchannel device.

Electrophoresis has become an indispensable analytical tool of the biotechnology and other industries, as it is used extensively in a variety of applications, including separation, identification and preparation of pure samples of nucleic acids, proteins, and carbohydrates; identification of a particular analyte in a complex mixture; and the like.

Of increasing interest in the broader field of electrophoresis is capillary electrophoresis ("CE"), where particular entities or species are moved through a medium in an electrophoretic chamber of capillary dimensions under the influence of an applied electric field. Benefits of CE include rapid run times, high separation efficiency, small sample volumes, etc. Although CE was originally carried out in capillary tubes, of increasing interest is the practice of using microchannels or trenches of capillary dimension on a planar substrate, known as microchannel electrophoresis ("MCE"). CE and MCE are increasingly finding use in a number of different applications in both basic research and industrial processes, including analytical, biomedical, pharmaceutical, environmental, molecular, biological, food and clinical applications.

Typically, the microchannels of MCE devices are constructed by forming troughs or grooves of appropriate dimension and configuration in one surface of a planar rectangular- or disc-shaped base substrate, and applying a planar cover to the surface to enclose the microchannels.

Conventionally, microchannels having capillary dimensions have been made in silicon or glass substrates by micromachining, or by employing photolithographic techniques. See, e.g., U.S. Pat. Nos. 4,908,112, 5,250,263. Where the substrates are of fused silica, the microchannels can be enclosed by anodic bonding of a base and a cover. Exemplary MCE devices are also described in U.S. Pat. Nos. 5,126,022; 5,296,114; 5,180,480; and 5,132,012; and in Harrison et al., "Micromachining a Miniaturized Capillary Electrophoresis-Based Chemical Analysis System on a Chip," Science (1992) 261: 895; Jacobsen et al, "Precolumn Reactions with Electrophoretic Analysis Integrated on a Microchip," Anal. Chem. (1994) 66: 2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348, Eckstrom et. al. U.S. Pat. No. 5,376,252 describes a process for creating capillary size channels in plastic using elastomeric spacing layers. Ohhman International Patent Publication WO 94/29400 describes a method for producing microchannel structures by applying a thin layer of a thermoplastic material to one or both of the surfaces to bejoined, then joining the surfaces and heating the joined parts to melt the thermoplastic bonding layer. Kaltenbach et al. U.S. Pat. No. 5,500,071 describes constructing a miniaturized planar microcolurn liquid phase analytical device by laser ablating microstructures in the surface of a planar laser ablatable polymeric or ceramic substrate, rather than by conventional silicon micromachining or etching techniques.

U.S. Pat. No. 6,176,962 describes methods for fabricating Mnicrochannel structures constructed of a polymeric card-shaped or disc-shaped base plate having a planar surface in which a microchannel structure is formed, and a planar polymeric cover. The microchannel structure is enclosed by bonding the planar surfaces of the cover and the base plate together.

SUMMARY OF THE INVENTION

In one general aspect, the invention features a continuous form microstructure (i.e., microcavity and/or microchannel) array device constructed as an elongate flexible film laminate containing a plurality of microstructures or arrays of microstructures arranged serially lengthwise along the laminate. Where the device has a series of microstmctures, each structure is configured to carry out a fluidic process or a step in a fluidic process. Where the device has a series of microchannel arrays, each array is configured to carry out a set of processes or steps, on an array of samples or of test reagents.

Because the microstructures, or arrays of microstructures, are serially arranged lengthwise along the laminate, the device can be fed lengthwise into and through an analytical device, and the structures or arrays can be treated serially in a continuous automated or semiautomated manner.

In some embodiments the flexible elongate laminate device is advanced within the analytic device from a continuous uncut supply roll, through the various parts of the analytical device and, as the laminate device is expended, to a takeup roll, similar to the way in which roll film is advanced frame-by-flame through a camera In other embodiments the elongate laminate device is advanced within the analytic device from a continuous uncut accordion-folded supply stack, through the analytical device and, as the laminate device is expended, to an accordion-folded takeup stack. When the entire roll (or supply stack) has been expended and passed onto the takeup roll (or stack), the expended roll (or stack) can be discarded, or can conveniently and efficiently be stored in an archive, as may be desirable for some uses.

The microstructures are constructed either by forming channels, trenches or cavities of suitable dimension and configuration in a microchannel surface of a first lamina and, optionally, enclosing the channels by apposing a covering surface of a second lamina onto the microchannel surface to form the microstructures; or by forming slits having suitable dimension and. configuration in a spacing lamina, and sandwiching the spacing lamina between first and second enclosing laminae to enclose the slits between the apposed surfaces of the first and second enclosing laminae to form the microchannels.

Electrodes can be formed in the device by any of a variety of techniques, known in the art, including application of wires or conductive decals, or printing or stamping using conductive inks, or vapor deposition, etc., in a specific configuration onto a surface of one or both of the laminae. The laminate construction according to the invention is particularly suitable for application of flexible printed circuit technology. For technical review, See, Th. H. Stearns (1996), Flexible Printed Circuitry, SMTnet Bookstore. See also, U.S. Pat. Nos. 4,626,462; 4,675,786; 4,715,928; 4,812,213; 5,219,640; 5,615,088.

Processes for making flexible printed circuits are generally well known. Briefly, the electrodes, which provide connections from the reservoirs in the microfluidic structure to high-voltage contacts in an analytical device that carried the laminate, are formed within a thin polymer film laminate, which serves as a cover lamina to be affixed as described above to the base lamina, as described in more detail below.

In this context, an "analytical device" is a device that includes at least a detector capable of detecting or of measuring a signal produced in the course of the microfluidic process or process step, and means for moving the laminate in relation to the analytical device to bring a detection region in the microstructure within the field of the detector. Usually the analytical device is in a stable installation, and the laminate is advanced through it past the detector, but in some embodiments the laminate is held in place and the analytical device is moved along it. Of course, any number of such detectors may be employed, each alignable with a detection region (or series of detection regions, as the laminate progresses through). Usually, the analytical device also includes electrical contacts each alignable with a contact point in electrical circuitry employed to generate electroflow in the microstructure. Each such contact is electrically connected to a source of electrical power, and to control means (which may be automated) for changing the applied electric fields as the microfluidic process proceeds. The analytical device may further include means for adding various fluids (e.g., samples, buffers or other solvents, reagents, and the like) to the microstructures by way of access ports in the laminate. The analytical device may additionally include means for changing the environmental conditions surrounding a portion of the laminate, such as temperature, and the like.

In some embodiments, the device is provided as an assembled laminate, in which the microchannels are fully enclosed; and in which ports or reservoirs are provided for introduction of sample or reagents or test compounds or liquid media; and in which electrodes have been emplaced and provided with leads for connection to a source of electrical power. Reagents, samples, test compounds, and/or media can be introduced as appropriate during or just prior to conducting the assays. In some embodiments the assembled laminate is provided with at least some of the media or reagents "on board" in the microchannels or reservoirs as appropriate. Where the device is provided with one or more substances already on board, the device can additionally be provided with means for protection of degradable contents from variations in ambient conditions and, particularly, for example, a release liner which resists loss of moisture or of volatile contents and/or which resists light exposure to the contents, may be provided as a release liner on one or both surfaces of the laminate.

The device and method of the invention provides a full range of advantages in analytical sensitivity that inhere in the use of conventional microfluidic analysis, while at the same time providing for automated or semiautomated continuous processing of high numbers of analyses at high rates of speed. The complexity of mass screening programs, for example, is substantially reduced by elimination of many of the manipulation steps, whether by hand or by machine, that are required in use of conventional assay plates. And possibilities for error are reduced by reduction of the number of points at which manipulation by hand is required.

Methods and apparatus according to the invention for carrying out multiple microfluidic manipulations at high throughput rates are readily adaptable for automated non-contact dispensing of reagents or samples, providing for substantially reduced risk of cross-contamination.

Further, the continuous form assay array according to the invention significantly reduces the bulk volume of disposable materials, as compared with conventional assay card methods, both because the flexible laminates themselves are thinner than are conventional assay cards, and because the microchannel structures or arrays can be arranged on the continuous form device with more efficient use of the substrate surface area.

BRIEF DESCRIPTION OF THE DRAWINGS

FIGS. 3A, 3B are diagrammatic sketches in plan view of two alternative embodiments of microchannel structures configured as standard injection crosses, in which the separation channel is curved (FIG. 3A) or folded (FIG. 3B) to provide extended separation flow path length.

FIG. 3C is a diagrammatic sketch in plan view of an embodiment of a microchannel structure providing for introduction of four reagents into a sample flow path upstream from the separation channel, which is folded to provide extended separation flow path length

FIG. 11a is a diagrammatic sketch of a portion of the length of an embodiment of a base lamina of a continuous form microstructure device of the invention, showing two in a series of microchannel arrays. Each microchannel array includes four microstructures each configured to carry out a receptor binding assay, as described with reference to FIG. 9.

FIG. 11b is a diagrammatic sketch of a portion of the length of flexible circuit laminate showing two in a series of layouts of electrodes and electrical contacts, each layout configured to serve a microchannel array as shown in FIG. 11a.

FIG. 11c is a diagrammatic sketch of a portion of the length of an embodiment of a continuous form elongate laminate microstructure device of the invention, constructed by laminating the flexible circuit laminate of FIG. 11b onto the base lamina of FIG. 11a.

Figure 1A:
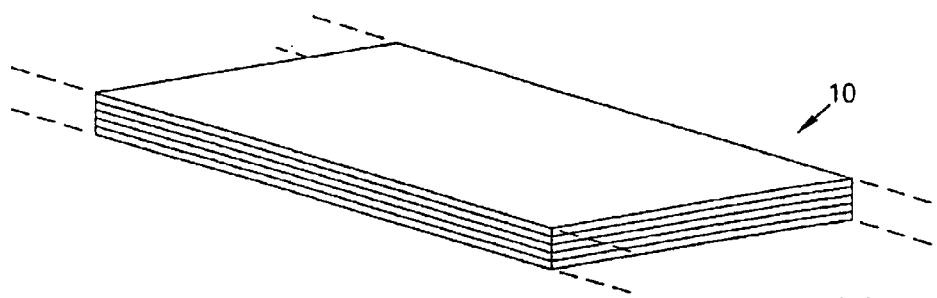
FIG. 1A is a diagrammatic sketch showing a portion of an embodiment of the laminate construction of a continuous form microchannel device of the invention.

The drawings are diagrammatic only and not to scale and, particularly, in some of the FIGS. the thicknesses of the laminate composites and of the layers of which they are constructed are much exaggerated for clarity of presentation.

DETAILED DESCRIPTION

Construction

In General

"Microfluidic processing", as that term is used herein, means and refers to fluid processing—that is, fluid handling, transport and manipulation—carried out within chambers and channels of capillary dimension. Valveless sample injection is achieved by moving fluid from reagent reservoirs into cross-channel injection zones, where plugs of buffer or test compounds are precisely metered and dispensed into a desired flowpath. The rate and timing of movement of the fluids in the various microchannels can be controlled by electrokinetic, magnetic, pneumatic, and/or thermal-gradient driven transport, among others. These sample manipulation methods enable the profile and volume of the fluid plug to be controlled over a range of sizes with high reproducibility. In addition, microfluidic processing includes sample preparation and isolation where enrichment microchannels containing separation media are employed for target capture and purification. Microfluidic processing also includes reagent mixing, reaction/incubation, separations and sample detection and analyses.

Generally, the expression "microstructure", as used herein, means and refers to a single enclosed microchannel or a network of interconnecting microchannels having cross-sectional dimensions suitable for carrying out microfluidic manipulations of materials carried by them. Several steps or stages of an analytical process may be carried out in one microchannel structure, suitably configured. Configurations of various complexity are disclosed for example in U.S. Pat. Nos. 5,900,130 and 6,007,690.

A "microfluidic network", as that term is used herein, is a system of interconnected microchannels, i.e., cavity structures and capillary-size channels, through which fluids can be manipulated and processed.

Cavity structures, in the context of microstructures, are spaces, usually formed in, e.g., a planar substrate, a plate, or the like in accordance with the present invention. Cavity structures include, e.g., wells, reservoirs, chambers for incubation or separation or detection, and the like. Cavity structures can be present at one or both of the termini, i.e., either end, of a channel, and are there usually referred to as reservoirs. Such cavities structures may serve a variety of purposes, such as, for example, means for introducing a buffer solution, elution solvent, reagent rinse and wash solutions, and so forth into a main channel or one or more interconnected auxiliary channels, receiving waste fluid from the main channel, and the like. In some embodiments, cavity structures are not connected by channels, but rather stand alone; such free standing cavities can be used for reagent introduction, on-board mixing, incubation, reactions, detection and the like. In another embodiment, these individual steps of a homogeneous assay can be carried out in a cavity.

In the microstructures of the invention "channels", usually "microchannels", provide conduits or means of communication (usually fluid communication and more particularly liquid communication), between cavity structures and the like. Channels include capillaries, grooves, trenches, microflumes, and so forth. The channels may be straight, curved, serpentine, labyrinth-like or other convenient configuration within the planar substrate. The cross-sectional shape of the channel may be circular, ellipsoidal, trapezoidal, square, rectangular, triangular and the like within the planar substrate in which it is present.

The inside of the channel may be coated with a material to improve the strength of the microstructure, for modifying, enhancing or reducing electroosmotic flow, for enhancing or reducing electrophoretic flow, for modification of surface hydrophobicity/hydrophilicity, for binding of selected compounds, and so forth. Exemplary coatings are silylation, polyacrylamine (vinyl-bound), methylcellulose, polyether, polyvinylpyrrolidone, and polyethylene glycol, polypropylene, Teflon™ (DuPont), Nafion™ (DuPont), polystyrene sulfonate and the like may also be used. See also U.S. Pat. No. 5,935,401, the relevant disclosure of which is incorporated herein by reference.

A "microchannel", as that term is used herein, is an at least partly enclosed trench or channel or cavity having capillary dimensions, that is, having cross-sectional dimensions that provide for capillary flow along the channel. Usually at least one of the cross-sectional dimensions, e.g., width, height, diameter, is at least about 1 $\mu$m, usually at least 10 $\mu$m and is usually no more than 500 $\mu$m, preferably no more than 200 $\mu$m. Channels of capillary dimension typically have an inside bore diameter ("ID") of from about 10 to 200 microns, more typically from about 25 to 100 microns.

Microchannels can provide for electroflow between cavity structures and the like in the microstructures of the invention. "Electroflow", as used herein, is the manipulation of entities such as molecules, particles, cells, vitreous fluid and the like through a medium under the influence of an applied electric field by use of electrodes and the like to induce movement such as electrokinetic flow, electroosmotic flow, electrophoretic flow, dielectrophoretic flow, and so forth. Depending upon the nature of the entities, e.g., whether or not they carry an electrical charge, as well as upon the surface chemistry of the chamber in which the electroflow is conducted, the entities may be moved through the medium under the direct influence of the applied electric field or as a result of bulk fluid flow through the pathway resulting from the application of the electric field, e.g., electroosmotic flow. It is within the purview of the present invention that electroflow can be carried out in conjunction with movement of material by other means than application of an electric field, such as by gravity or by application of a magnetic field, centrifugal force, thermal gradients, aspiration, negative pressure, pumping, pneumatic forces, and the like.

An "electroflow medium" is an electrically conductive medium, that is generally utilized in carrying out microfluidic processes. The particular medium chosen is one that is suitable to a particular application of the present invention. Such media include, for example, buffer solutions, cross-linked and uncross-linked polymeric solutions, organic solvents, detergents, surfactant micellular dispersions, gels of the type generally used in connection with analytical separation techniques and other microfluidic processes, and so forth. For example, cross-linked polyacrylamide gel, cellulose derivatives, uncross-linked polyacrylamide and derivatives thereof, polyvinyl alcohols, polyethylene oxides and the like may be used. For a discussion of such media see, e.g., Barron and Blanch, "DNA Separations by Slab Gel and Capillary Electrophoresis: Theory and Practice", Separation and Purification Methods (1995) 24:1–118.

Suitable electroflow media include conventional buffers such as, for example, the Good's buffers (HEPES, MOPS, MES, Tricine, etc.), and other organic buffers (Tris, acetate, citrate, and fornate), including standard inorganic compounds (phosphate, borate, etc.). Exemplary buffer systems include: (i) 100 mM sodium phosphate, pH 7.2; (i) 89.5 mM tris-base, 89:5 mM Boric acid, 2 mM ETDA, pH 8.3. Buffer additives include: methanol, metal ions, urea, surfactants, and zwitterions, intercalating dyes and other labeling reagents. Polymers can be added to create a sieving buffer for the differential separation of molecular species, such as, e.g., nucleic acids, proteins, and the like, based on molecular size. Examples of such polymers are: polyacrylamide (cross-linked or linear), agarose, methylcellulose and derivatives, dextrans, and polyethylene glycol. Inert polymers can be added to the separation buffer to stabilize the separation matrix against factors such as convective mixing.

Alternatively, buffers containing micelles can be used for effecting separation of electrically neutral or hydrophobic substances of interest. The micelles are formed in the buffer by addition of an appropriate surfactant at a concentration exceeding the critical micelle concentration of that detergent. Useful surfactants include but are not limited to sodium dodecyl sulfate, dodecyltrimethyl ammonium bromide, etc. Weakly charged or apolar analytes partition into the micelles to different degrees depending upon their degree of hydrophobicity and thus can be separated. This subtechnique of capillary electrophoresis is termed micellar electrokinetic chromatography.

"Electrophoresis" is separation of components in a liquid by electroflow. Various forms of electrophoresis include, by way of example and not limitation, free zone electrophoresis, gel electrophoresis, isotachophoresis, high performance CE, capillary zone electrophoresis, and the like. In the context of the microstructures according to the invention, an "electrophoresis column" is a channel for carrying out electrophoresis.

A microstructure can be made by forming one or more trenches or channels or cavities in the desired configuration and with the desired dimensions in one surface of a lamina, and then optionally covering selected portions at least of the trenches or channels or cavities with a second lamina to form one or more enclosed microchannels. Or, a microstructure can be made by forming slits in the desired configuration and with the desired dimensions through a spacing lamina having a desired thickness, and then enclosing selected portions at least of the slits by sandwiching the spacing lamina between two enclosing laminae to form one or more enclosed microchannels.

As noted above, the enclosed volumes within the microchannels provide "flow paths", in which the various components of the analytical process can move and combine and interact or react, and in which analytes can be separated electrophoretically or retained by capture media Any of a variety of means can be employed to provide sources of supply of the various components to the flow paths.

Any of a variety of means can be employed to cause movement of the various components within the microchannels. Usually, as noted above, an electric field is applied to a segment of a microchannel to cause electrokinetic transport (by electroosmotic flow or by electrophoresis, or by some combination of EOF and electrophoresis) of the contents of the microchannel segment. An electric field can be applied by positioning a pair of electrodes, connected to a source of electrical power, within the microchannel at the ends of the microchannel segment. Where it is desired, for example, to move a buffer from a buffer reservoir along a microchannel to a buffer waste reservoir, the pair of electrodes can be positioned so that they contact the fluid within the respective reservoirs; application of an electric potential across the electrodes induces a electrokinetic flow from one reservoir to the other through the micro channel.

Additionally, as noted above, other means than electrokinetic flow may be used to move the components within the microchannels, and, particularly, to fill the microchannel structure at the outset, or to introduce an aliquot of sample material or of a test compound, for example, at the beginning of or in the course of the analysis.

As used herein, the expression "array of microchannel structures" means and refers to a set of microchannel structures, typically but not necessarily all having the same or similar configurations, each operating to carry out one of a set of related analyses, as will be described more fully below. A microstructure or an array of microstructures can according to the invention be arranged within the laminate structure so that the positions of various of the cavities correspond to particular useful sites in conventional sample holding or sample delivery apparatus. Thus, for example, certain of the cavities may be arranged and spaced apart to correspond to the dimensions and configurations of a standard multiwell plate, which has an array of wells. Standard plates may have any number of wells, usually in a patter, and usually numbering 96, 192, 384 or 1536 wells or more. Examples of such multiwell plates are microtiter plates having a pattern of wells. The wells extend into the substrate forming the plate, and are open at the top surface of the plate and closed at the bottom. There are no openings, holes or other exits from the wells other than, from the top surface at the opening of the well. Similarly, a transfer plate may have a like arrangement of apertures or nozzles, and at least selected ones of the cavities in the microstructure or microstructure array according to the invention can accordingly be arranged so that direct transfer can be made from the plate to the microcavity network.

Other arrangements for the arrays of microchannel structures are possible, according to the particular dispensing requirements, among other factors. For example, an array of 96 microstructures may be in a 12×8 orthogonal arrangement, corresponding to the positions of wells in a 96-well microtiter plate; or in a linear arrangement of 96 microstructures, or any other arrangement. And, an array of 384 microstructures may be in a 24×16 orthogonal arrangement, corresponding to the positions of wells in a 384-well microtiter plate; or in a linear arrangement of 384 microstructures, or any other arrangement.

Depending upon the type of analysis to be performed, any of various liquid media including buffers or solvents or electrophoretic separation media, reagents, etc., may be brought into play in the course of the analysis.

At one or more points in the analytical process, detection and/or measurement of one or more analytes is required. The analyte or analytes may be, for example, a plurality of electrophoretically resolved reaction products, such as restriction fragments of a nucleic acid, bound and free fractions in a ligand-binding assay, substrate and product of an enzymatic reaction, and the like.

The Laminate

Figure 1B:
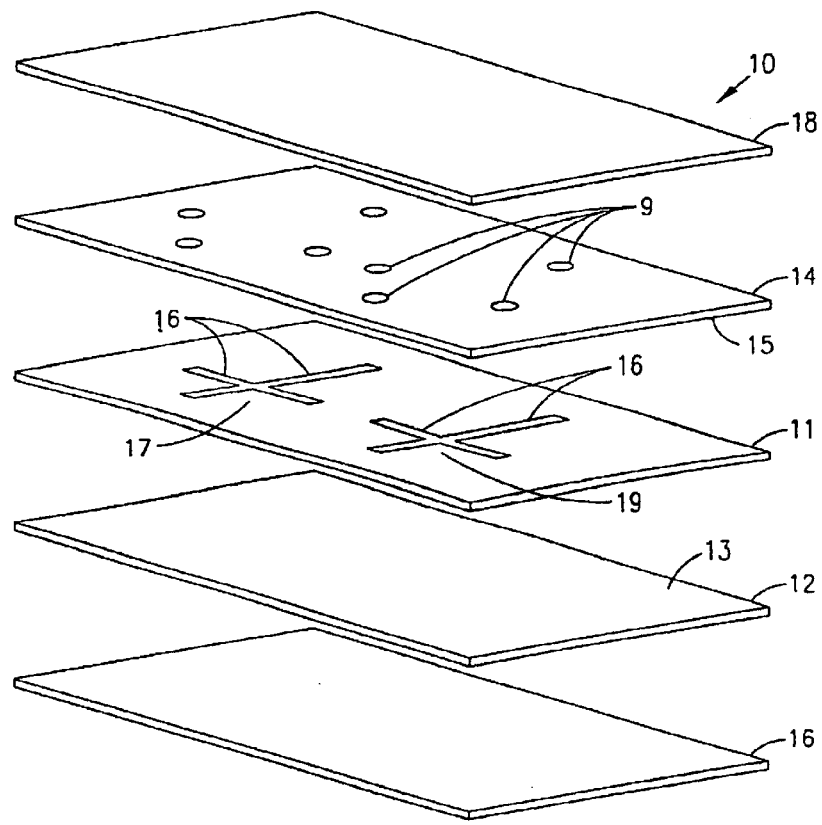
FIG. 1B is a diagrammatic sketch of the portion of the embodiment of FIG. 1A, in an exploded view, showing the laminae.

Referring now to FIGS. 1A, 1B, there is shown at 10 a portion of an embodiment of an elongate flexible film laminate according to the invention, as assembled (FIG. 1A) and in an exploded view in which the laminae appear as separated (FIG. 1B). In FIGS. 1A and 1B, as in FIGS. 2A, 2B, only a short segment of the full length of the laminate is shown, as suggested by broken lines indicating that the laminate extends lengthwise beyond the margins of the drawing. In the embodiment of FIGS. 1A, 1B, the microchannel structure is formed in a spacing lamina 11 sandwiched between a base lamina 12 and a cover lamina 14, Slits 16 having capillary cross-sectional dimensions are formed through spacing lamina 11, and are enclosed by apposed surfaces 13, 15 of base lamina 12 and cover lamina 14 in the composite structure. FIG. 1B shows slits forming walls of just two 17, 19 of many microchannel structures serially arranged lengthwise on the elongate laminate. In the example shown in FIGS. 1A, 1B, each microchannel structure has a simple cross configuration formed by enclosure of a pair of intersecting slits.

As will be appreciated, the widths of the microchannels resulting from the construction illustrated in FIGS. 1A, 1B is established by the width of the slits in the spacing lamina; and the thickness of the microchannels is established by the distance between the apposed surfaces 13, 15 of the enclosing laminae 12 and 14, which approximates the thickness of the spacing layer. As noted above, the microchannels are of capillary dimension, that is, the larger cross-sectional dimension (usually the width) of the microchannel is usually no greater than about 750 $\mu$m, more usually no greater than about 500 $\mu$m, and most usually in the range from about 100 $\mu$m to about 250 $\mu$m; and the smaller cross-sectional dimension (usually the depth) can be somewhat smaller.

Usually, as noted generally above, reservoirs or access ports or receptacles are provided for introducing the various components of the analytic process (sample, buffers or solvents, test compounds, etc.) into the microchannel structures. These can be in the form, for example, of perforations 9 through the base lamina 12 or through the cover lamina 14, as illustrated in FIG. 1B. Where, as shown for example in FIG. 1B, the reservoirs or access ports or receptacles are formed in a lamina other than the one in which the channels are formed, they must be located so as to be suitably aligned with appropriate sites in the microchannel structure when the composite is assembled. Accordingly, in FIG. 1B, the perforations 9 in the cover lamina 12 are arranged to be aligned with the ends of the microchannels formed in the spacing layer 11 when the spacing lamina 11 is sandwiched between the apposed surfaces 13, 15 of the base lamina 12 and the cover lamina 14.

To provide for predictable and consistent microfluidic movement, mixing, and separations, the microchannels in the laminate composite device must be adequately dimensionally stable, and the apposing surfaces 13, 15 of the enclosing laminae 12, 14 must be adequately sealed to the surfaces of spacing lamina 11, at least at the margins of the slits, to keep the fluids within the flow paths formed by the microchannels from escaping between the laminae. These requirements are met by appropriate selection of materials and thicknesses of the films making up the laminae, and by appropriate selection of means for sealing the contact surfaces of the laminae.

As noted above, each of the laminae is a flexible film, usually firm enough to hold shape and dimensions of the microchannels, yet sufficiently compliant to provide flexibility in the composite laminate device. Preferred films include acrylics and polyethylenes, for example. Preferred means for sealing will be selected according to the film materials in the laminae to be joined. Particularly, for example, the film material and adhesives described in U.S. Pat. No. 6.176,962, the disclosure of which is hereby incorporated herein in its entirety.

In the embodiment of FIGS. 1A, 1B, the thickness of the spacing lamina is selected to provide the desired microchannel depth, taking into account any effect (additive or subtractive) that the sealing process may have on the distance between the apposed surfaces 13, 15 of the enclosing laminae.

In addition to the spacing lamina 11 and the enclosing laminae 12, 14, the laminate may further include release liners 16 and/or 18, Use of a release liner may be especially desirable where at least some of the components of the analytical process (a reagent or a buffer, for example) are provided on board the device prior to use. Such release liners can mitigate degradation or loss of the contents of the device during prolonged exposure to varying environmental conditions that may be encountered prior to use of the device, as for example during storage. It may be particularly important, for example, to avoid loss or intrusion of moisture or of more volatile substances out from or into the microchannel structure. Or, it may be important to avoid exposure to light. Accordingly, preferred release liners form a barrier to movement of moisture or volatile materials, and thin polymer films, including metallized films may be particularly suitable.

Figure 2A:
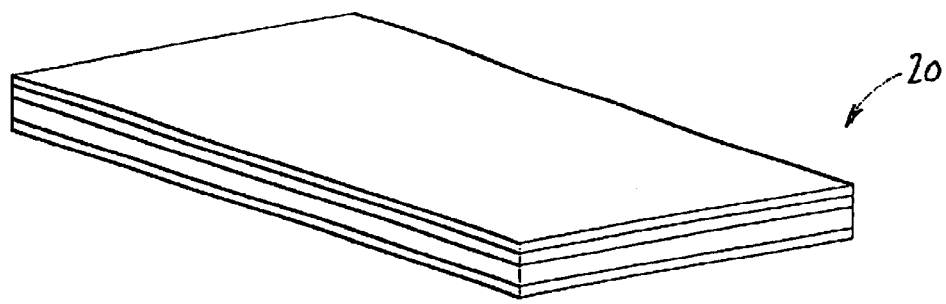
FIG. 2A is a diagrammatic sketch of a portion of an alternate embodiment of the laminate construction of a continuous form microchannel device of the invention.
Figure 2B:
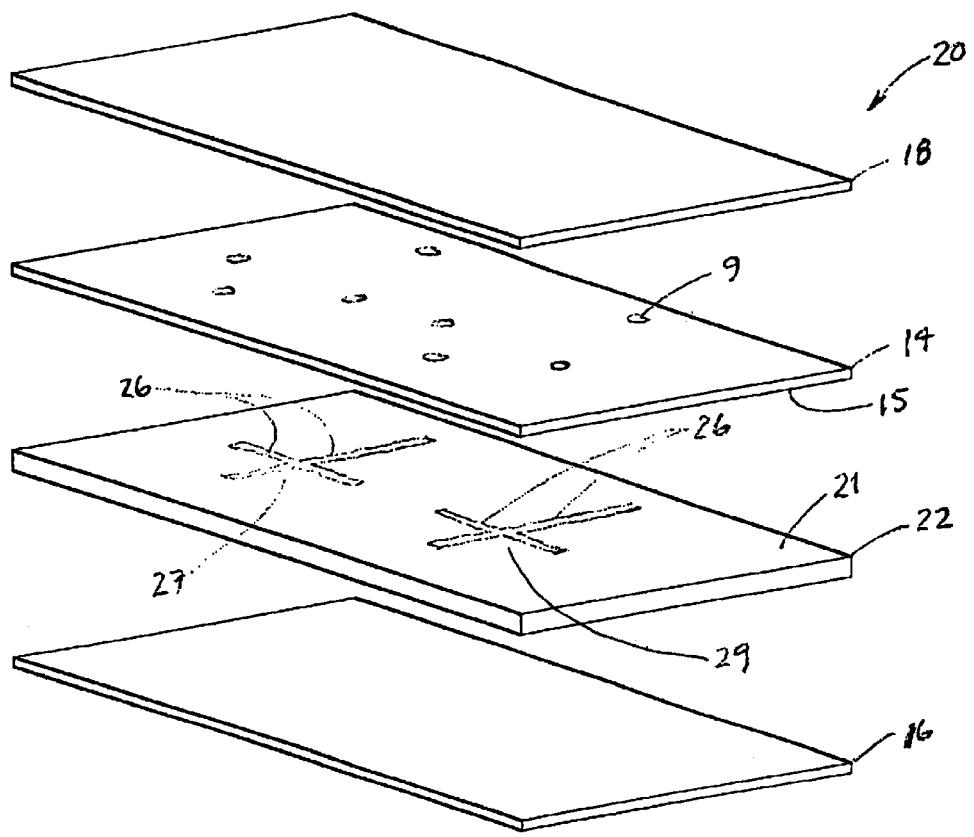
FIG. 2B is a diagrammatic sketch of the portion of the embodiment of FIG. 2A, in an exploded view, showing the laminae.

Referring now to FIGS. 2A, 2B, there is shown at 20 a portion of an alternate embodiment of an elongate flexible film laminate according to the invention, a assembled (FIG. 2A) and in an exploded view in which the laminae appear as separated (FIG. 2B). In this embodiment, the microchannel structure is constructed by forming channels or trenches 26 in a surface 21 of base lamina 22, and apposing a surface 15 of a cover lamina 14 onto surface 21 to enclose the microchannels. Reservoirs or access ports or receptacles can be provided for introduction of process components into and/or for removal of excess or waste from the microchannel structure, as noted with reference to FIGS. 1A, 1B. These are illustrated by way of example in FIG. 2A as perforations 9 through cover lamina 14, positioned so as to be suitably aligned with the channels or trenches 26 in the base lamina 22 when the surfaces 21, 15 of base lamina 22 and cover lamina 14 are apposed.

Alternatively, reservoirs may be provided in base lamina 22, in the form of wells or holes through the thickness of base lamina 22, each situated in fluid communication with a microchannel or trench, as may be desired. And, referring again to FIGS. 1A, 1B, reservoirs may be provided in the spacing lamina 11, each in fluid communication with a slit. If the base lamina 22 (or the spacing lamina 11) is sufficiently thick, reservoirs of significantly high volume can be provided in this way, and the cover lamina (or enclosing laminae) can be very thin. For reservoirs that are loaded in the course of the lamination process, no access opening through either the cover lamina or the opposite surface of the base lamina (or either of the spacing laminae) is required; however, for any such reservoirs that are to be loaded after the laminate has been formed, access openings aligned with the reservoirs can be provided, for example as holes through the cover lamina or through the base lamina (or through a spacing lamina).

In this embodiment the widths and depths of the microchannels are established by the dimensions of the trenches or channels formed in the base lamina. Accordingly, precise control of the dimensions during the formation of the trenches or channels, taking account of any additive or subtractive effect of the sealing process, results in reproducible microchannel dimensions.

As in the embodiment of FIGS. 1A, 1B, the embodiment of FIGS. 2A, 2B may additionally include release liners 16 and/or 18.

As in the embodiment of FIGS. 1A, 1B, each of the laminae in the embodiment of FIGS. 2A, 2B is a flexible film. Preferred film materials for the base lamina 22 and cover lamina 14 are polymer films; and preferred sealing means are selected according to the film materials to be joined. The base lamina 12 preferably is sufficiently thick to maintain its structural integrity after the trenches or channels have been formed in it. Particularly, for example, where the configuration of the microchannel structure is complex, or where there is a high density of trenches or channels, the mechanical strength of the base lamina may be compromised, and for ease of handling as well as to maintain the dimensionality of the microchannel structure during assembly and use, the base lamina should be thick enough so that it maintains its mechanical integrity.

Detection is usually optical, and most usually the signal is generated by laser-induced fluorescence; the detector is usually a conventional confocal optical system. Other detections means may be employed.

As noted above, each of the microchannel structures shown in FIGS. 1B, 2B is configured as a simple injection cross, formed by intersection of two straight microchannels. Such a configuration is useful, for example, in carrying out a quantitative electrophoretic separation of a metered sample volume, as described for example in U.S. Pat. No. 6,007,690 [SOAN-017]. The intersecting microchannels of a simple injection cross need not be straight, and in some configurations more efficient use of the substrate area is made possible by configuring one or more microchannel arms otherwise. Referring now for example to FIGS. 3A, 3B, alternative embodiments of simple injection cross configurations are shown in which one electrophoretic microchannel is made relatively longer. In each of microchannel structure configurations 30, 32, a shorter microchannel and a longer microchannel intersect at 31 to form an injection cross. Sample supply reservoir 36, sample drain reservoir 37, elution buffer reservoir 33, and analyte waste reservoir 34 are provided at the ends of the microchannel segments; and an electrode (not shown in the FIGS.) connected to a source of electrical energy is positioned to contact the liquid contained within each reservoir. Potential differences across the electrodes are adjusted first to draw the sample electrokinetically from sample supply reservoir 36 across art intersection 31 toward sample drain reservoir 37; and then to draw a metered volume of sample from intersection 31 into separation channel 35, As the sample plug proceed electrokinetically through separation channel 35 toward analyte waste reservoir 34, the sample becomes electrophoretically separated into its analyte components, which are detected at a downstream detection region point in separation channel 35, As will be apparent in the Figs., the electrophoretic separation channel is made relatively much longer by forming it as a spiral turning one or more times around intersection 31 and reservoirs 33, 36, 37, and the shorter microchannel arms (FIG. 3A), or by forming it in a folded configuration (FIG. 3B). The resulting microchannel structures occupy a compact area of the substrate, and can be particulay useful in microchannel arrays, as will be described more fully below with reference to FIG. 4.

The microchannel structures can be formed in more complex configurations, according to the analytical process to be carried out in them. Referring now to FIG. 3C, there is shown by way of example at 38 a microchannel structure having an intersection 31 forming an injection cross, and having sample supply reservoir 36, sample rain reservoir 37, elution buffer reservoir 33, and extended electrophoretic separation channel 35 leading to waste reservoir 34, In this embodiment, microchannels enclosing flow paths running from four additional supply reservoirs 39 to four additional downstream drains 40 additionally cross the microchannel downstream from the intersection 31, These additional flow paths provide for sequential introduction of four additional analytical components (which may be reagents, or test compounds, or buffers, etc.) to the moving sample plug.

Figure 4:
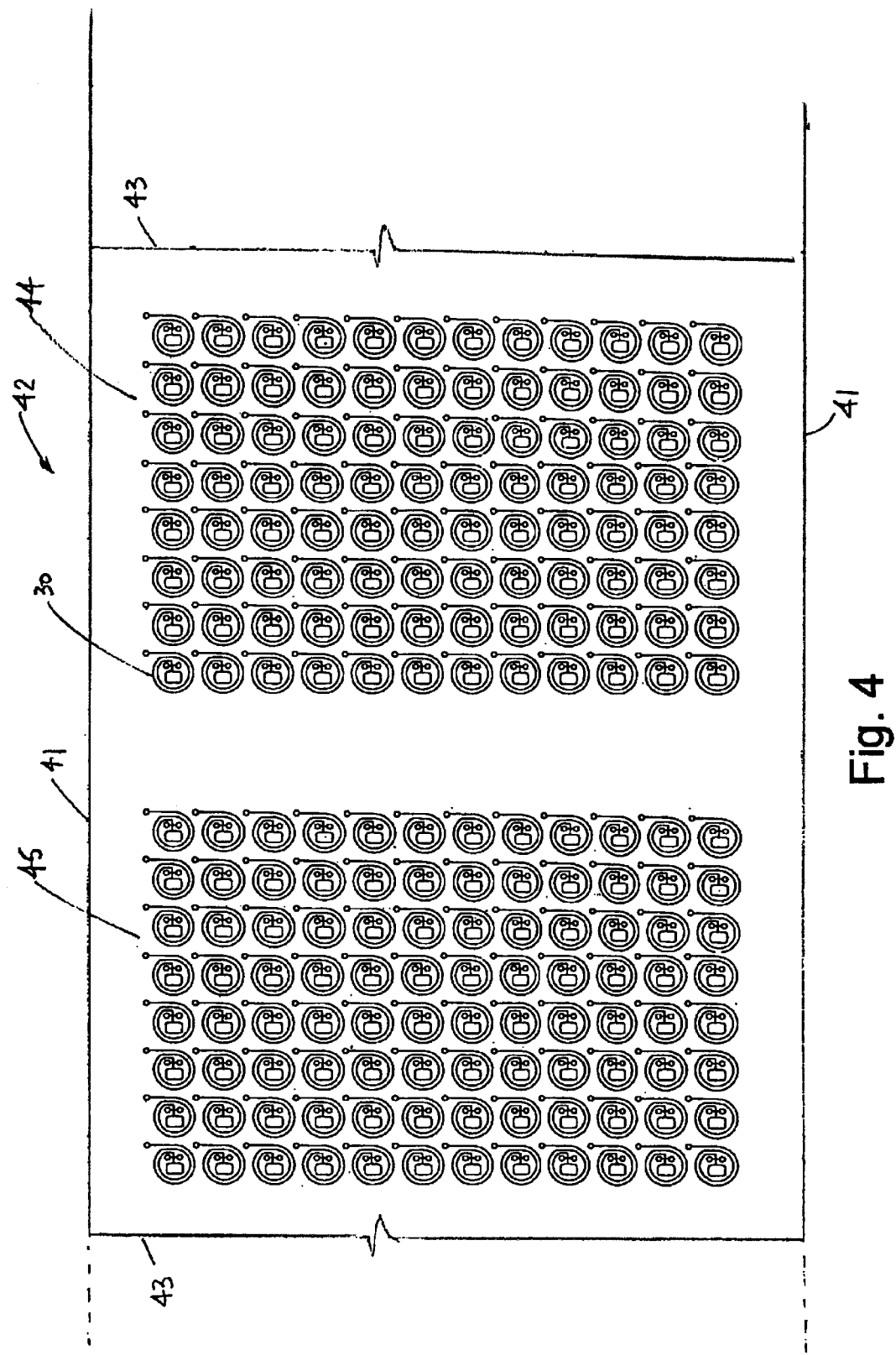
FIG. 4 is a diagrammatic sketch in plan view of a portion of the length of an embodiment of a continuous form microchannel device of the invention, showing two in a series of microchannel arrays.

An example of a microchannel array is shown in a plan view in FIG. 4, illustrating a way in which the arrangement of the microchannels structures in the array can be made to match the geometry of, for example, a standard 96-well plate. Such an arrangement can facilitate automated transfer of samples or of test compounds from the standard plate to the continuous form microchannel device of the invention, providing for efficient transfer with reduced waste and minimal cross-contamination. FIG. 4, for example, shows a short segment of an elongate flexible film laminate containing a series of microchannel arrays according to the invention. The elongate flexible film laminate 42 extends lengthwise beyond the range of the drawing, as indicated by broken lines extending from the edges 41 of the short segment. The short segment shown, which is limited by lines 43, includes two successive microchannel arrays 44, 45, Each of the microchannel arrays 44, 45 in this example contains 96 microchannel structures 30, each configured as in the example shown in FIG. 3A, and all arranged in an orthogonal 12×8 grid that conforms to the geometry of a conventional 96-well plate.

Manufacture

The basic technique and machinery for bringing the laminae together to form the laminate composite according to the invention are generally known, and, depending upon the materials that make up the various laminae, any of a variety of film lamination techniques can be used.

Figure 5:
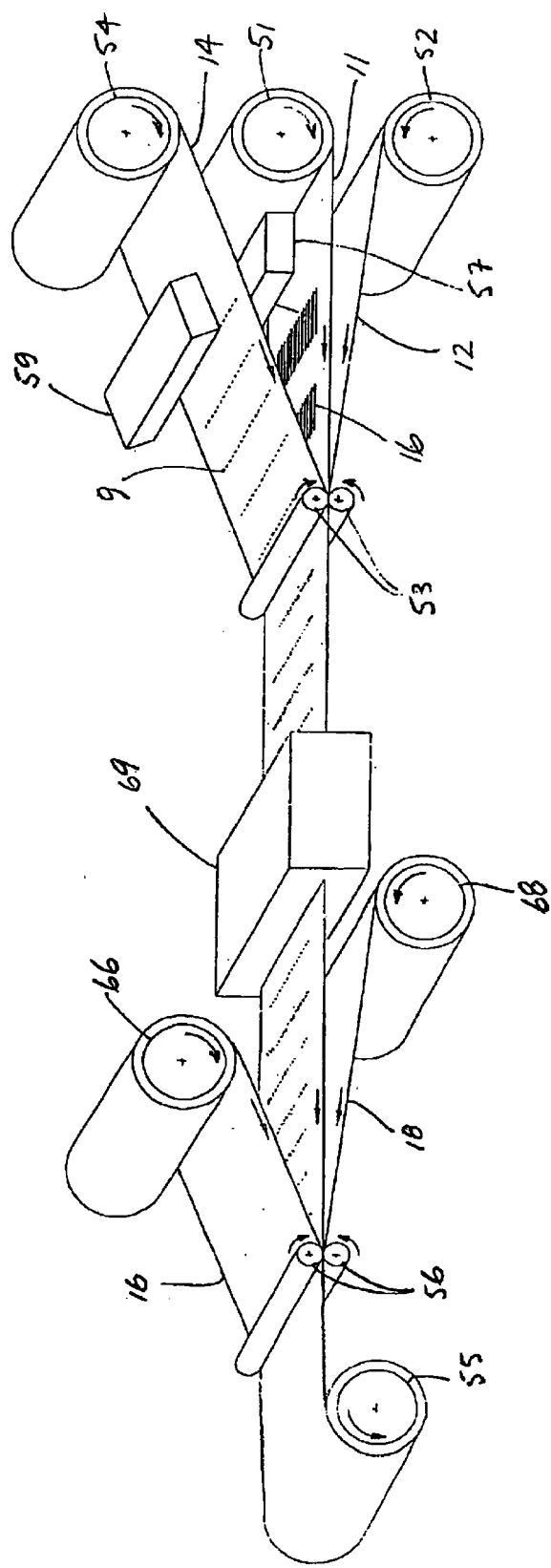
FIG. 5 is a diagrammatic sketch in a perspective view showing a method for constructing an elongate flexible film laminate having the general laminate structure shown in FIG. 1A.
Figure 6:
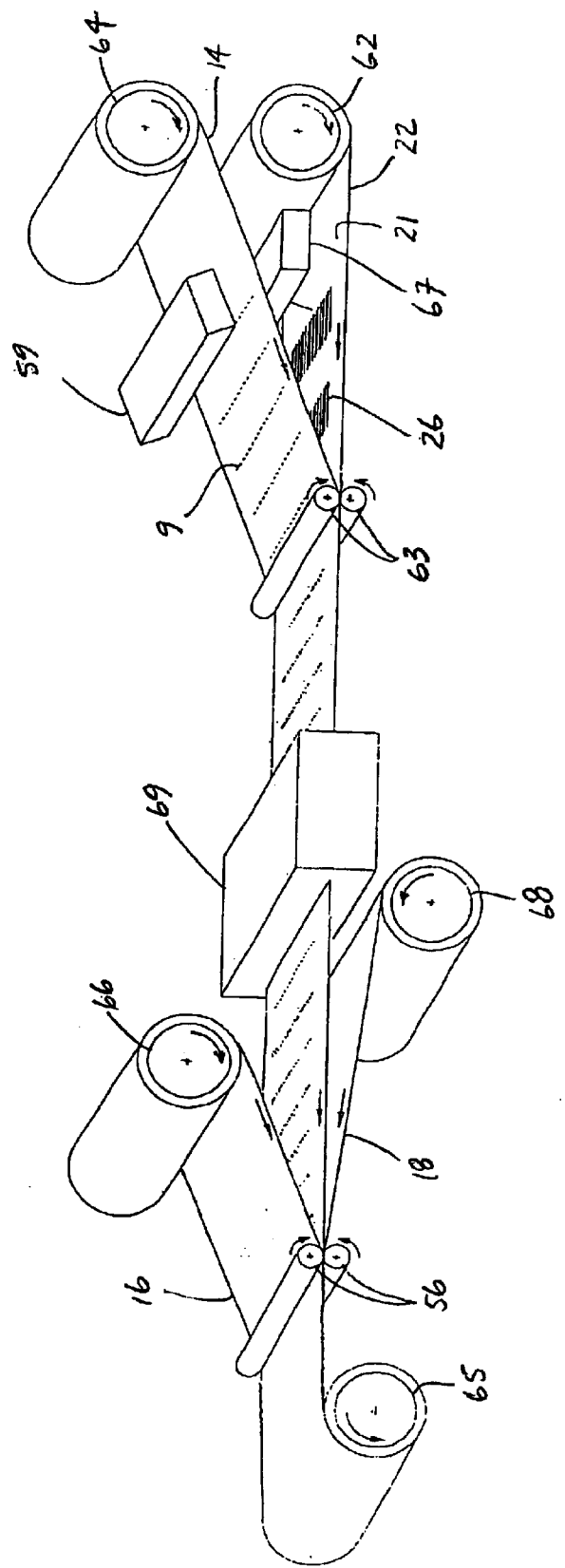
FIG. 6 is a diagrammatic sketch in a side view showing a method for constructing an elongate flexible film laminate having the general laminate structure shown in FIG. 2A.

FIGS. 5 and 6 are sketches showing in general outline schemes for constructing the laminate embodiments of FIGS. 1A and 2A. Referring now to FIG. 5, there are shown rollers 51, 52, and 54, carrying film materials to serve as, respectively, a spacing lamina 11, a base lamina 12, and a cover lamina 14. Slits 16 may be cut through spacing lamina 11 before it is rolled onto roller 51, so that the spacing lamina comes off roller 51 with the configuration of the microchannel structures already in place; or, as illustrated in FIG. 5, a cutting tool 57 may operate to cut the slits in the predetermined pattern as spacing lamina 11 is drawn from roller 51, Similarly, access openings or reservoirs 9 can be formed by perforating base larnina 12 or (as in FIG. 5) cover lamina 14 before it is stored on roller 54, so that during assembly the cover lamina comes off roller 54 with the perforations already in place; or, as illustrated in FIG. 5, a cutting tool 59 may operate to cut the predetermined pattern of perforations as cover lamina 14 is drawn from roller 54, In either method, preferred tools for cutting slits and perforations include lasers (laser cutting or laser ablation) and die cutting, for example.

Laminae 11, 12, and 14 are apposed by drawing them between rollers 53. As will be appreciated, it is essential that the perforated enclosing lamina be appropriately aligned with the spacing lamina during the lamination process, so that the perforations will be suitably aligned with the microchannels in the assembled device. Any registration technique may be used to ensure proper alignment in the longitudinal direction. Preferably, sprocket holes can be cut in one or both margins of the laminae, and the respective sprocket holes can be aligned on a sprocket. It can be suitable to provide a sprocket drive at the rollers 53, for example.

As noted generally above, certain of the components of the analytic process to be carried out in the device (buffer or solvent, separation media, etc.) can be loaded into portions of the microchannel structure before use. Particularly, it may be desirable to load certain of the constituents before enclosing the microchannels. This may be true, for example, if one or more constituents has a high viscosity at ambient temperatures, as may be true of certain electrophoretic separation media. Accordingly, as illustrated in FIG. 5, the assembled laminate formed of the spacing layer 11 enclosed by base layer 12 and cover layer 14 is drawn through a filling workstation 69, by conventional tractor means, where the selected components are injected or drawn by suction into the appropriate microchannels by way of the access perforations.

And, as noted above, where one or more components are provided on board the device, it maybe desirable to seal one or both surfaces of the device with release liners. Accordingly it is optional, as shown in FIG. 5, as the assembled and filled laminate is drawn toward takeup roller 55, to draw release liners 16 and 18 from rollers 66, 68 and between rollers 56, to appose the release liners onto the surfaces of the enclosing laminae 12 and 14, Alternatively, where the nonperforated enclosing layer is impermeable to the contents of the assembled and filled microchannel laminate of spacing layer 11 and enclosing layers 12, 14, sufficient protection of the contents can be provided by the contact of the nonperforated surface and the perforated surface when the device is rolled onto takeup roller 55, on which the device can be stored for use.

Similarly, referring now to FIG. 6, there are shown rollers 64, 62, carrying film materials to serve as, respectively, a cover lamina 14 and a base lamina 22, Channels or trenches 26 may be formed in surface 21 of base lamina 22 before it is rolled onto roller 62, so that the base lamina comes off roller 62 with the configuration of the microchannels already in place; or, as illustrated in FIG. 6, a cutting tool (or other means, as described in more detail below with reference to FIGS. 7 through 9) 67 may operate to form the trenches or channels in the predetermined pattern as base lamina 22 is drawn from roller 62. Suitable cutting techniques employ, for example, controlled laser ablation, using equpment and techniques well known in the laser micromachining industry. Suitable laser micromachining systems and protocols for their use are available from, for example, Resonetics, Nashua, N.H.

Other means for forming channels, cavities or trenches include but are not limited to heat embossing, UV embossing, or hot stamping a surface of a film layer prior to lamination. Known micromachining techniques including. e.g., photolithographic techniques, may also be employed in forming the microstructures in the film surfaces. Alternative methods also include ultrasonic forming, pressure forming and thermal forming, vacuum forming, blow molding, stretch molding, insert molding, encapsulation processes, any of which may be employed in a continuous-form process according to the invention. Any suitable techniques such as are known in the plastics micromachining art may be employed.

Similarly, access openings or reservoirs 9 can be formed by perforating cover lamina 14 before it is stored on roller 64, so that during assembly the cover lamina comes off roller 64 with the perforations already in place; or, as illustrated in FIG. 6, a cutting tool 59 may operate to cut the predetermined pattern of perforations as cover lamina 14 is drawn from roller 64, In either method, preferred tools for perforating the cover lamina include lasers and die cutters, for example, as described above with reference to FIG. 5, for example.

Laminae 14 and 22 are apposed by drawing them between rollers 63, and properly aligned as described above with reference to FIG. 5.

Here, as in the embodiment of FIG. 5, the assembled device can be provided with one or more of the analytical components on board. Components can be loaded into the assembled device by drawing the assembled laminate formed of the base layer 22 and the cover layer 14 through a filling workstation 69, as described above with reference to FIG. 5. And, optionally where desired, as the assembled and filled laminate is drawn toward takeup roller 65, release liners 16 and 18 may be drawn from rollers 66, 68, and between rollers 56, to appose the release liners onto the surfaces of the laminate for protection.

In some embodiments according to the invention, the reservoir and microchannel are formed in the base lamina, and the flexible circuit laminate forms a cover lamina. In one approach, illustrated in FIGS. 7a and 7b, the flexible circuit laminate (that is, the cover lamina) is made up of two layers, namely, a seal layer and a back layer. In this embodiment part of the conductive trace is formed on the back surface of the seal layer, and part is formed in the front surface of the back layer. In another approach, illustrated in FIGS. 8a and 8b, the flexible circuit layer is made up of three layers, namely a seal layer, which carries no conductive trace, and two circuit layers, each carrying a conductive trace. One of these circuit layers is a back layer, and the other is laminated between the back layer and the seal layer.

Figure 7A:
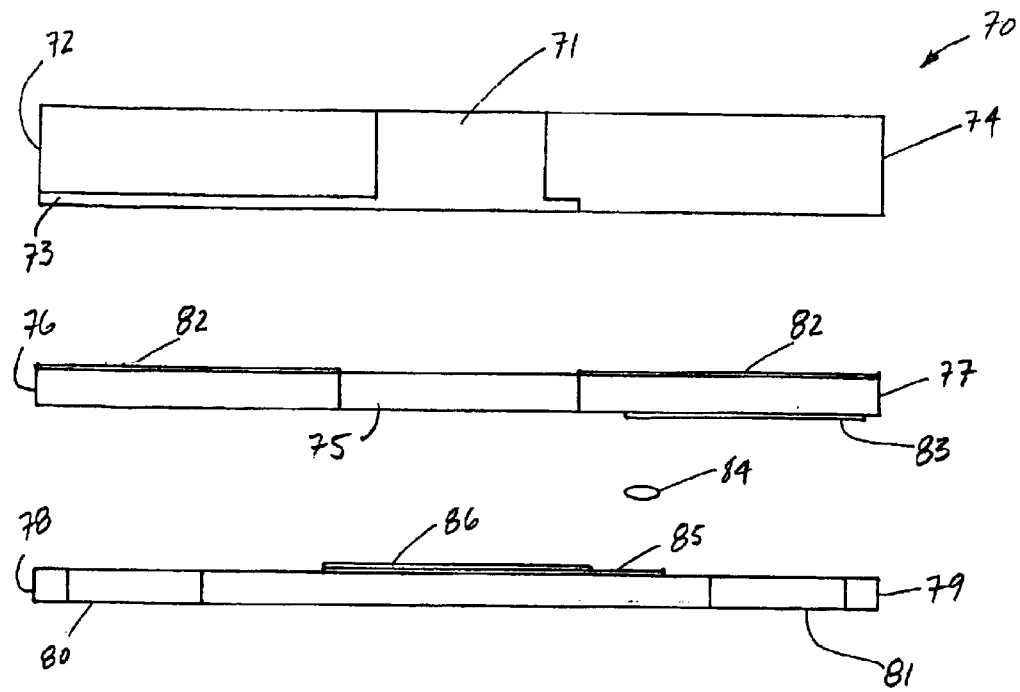
FIGS. 7a, b are diagrammatic sketches in sectional view showing details of an embodiment of a device according to the invention made using a flexible circuit lamina.
Figure 7B:
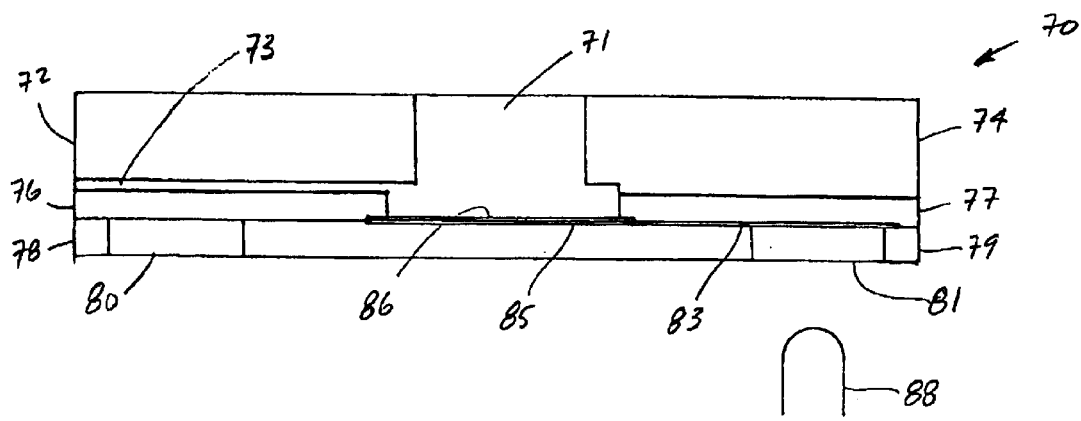

Referring now to FIGS. 7a, 7b, there is shown generally at 70 a portion of a device according to the invention, in transverse section thru a reservoir and microchannel and associated circuitry. The device consists of a base lamina 72, constructed of a generally planar plastic material 74, a seal layer 76, formed of a low fluorescence polymer film 77, and a back layer 78, formed of a plastic film 79, Formed in the polymer base lamina 74 are reservoir 71 and microchannel 73, An opening 75 is formed through the seal layer film 77 in register with the reservoir 71, A front surface of seal layer film 77 is provided with an adhesive 82, which will serve to seal the seal layer and the base layer together when assembled, as shown in FIG. 7b. A rear surface of the seal layer is provided with contact conductive trace portion 83 of the circuitry. A detection clearance opening 80 is formed through back layer film 79 in register with a detection zone of the microchannel 73, and a contact opening 81 is formed through back layer film 79 in register with the contact conductive trace portion 83, A front surface of the back layer film 79 is provided with a second conductive trace 85, having one region in register with a region of the contact conductive trace 83 and another region in contact with a carbon electrode 86, which in turn is in register with the reservoir 71. A conductive adhesive 84 provides for good conductive adhesion between conductive traces 83, 85, when assembled, as shown in FIG. 7b. Referring now to FIG. 7b, an electrical contact 88 in the analytical instrument contacts the conductive trace portion of the circuitry by way of the contact opening in the back layer, and a photodetector (not shown in the Figs.) detects the signal in the microchannel through the low fluorescence film of the seal layer by way of the detection opening 80 in the back layer.

Where laser-induced fluorescence detection is employed, preferred low fluorescence materials have sufficiently low fluorescence at the illuminating and back scattering wavelengths that the presence of the film in the optical path does not significantly reduce detection. Examples of suitable such materials include impact modified acrylic (e.g., Rohm film 99530), polyethylene terephthalate ("PET"), polyolefins (e.g., Zeonex), and acetates. The adhesive also preferably has low fluorescence characteristics, and preferably has surface characteristics similar to those of the walls of the channel, inasmuch as the adhesive will form one inner surface of the microchannel when assembled, and differences could a diversely affect electroflow in the channel. Suitable such adhesives include organic based acrylic adhesives.

Figure 8A:
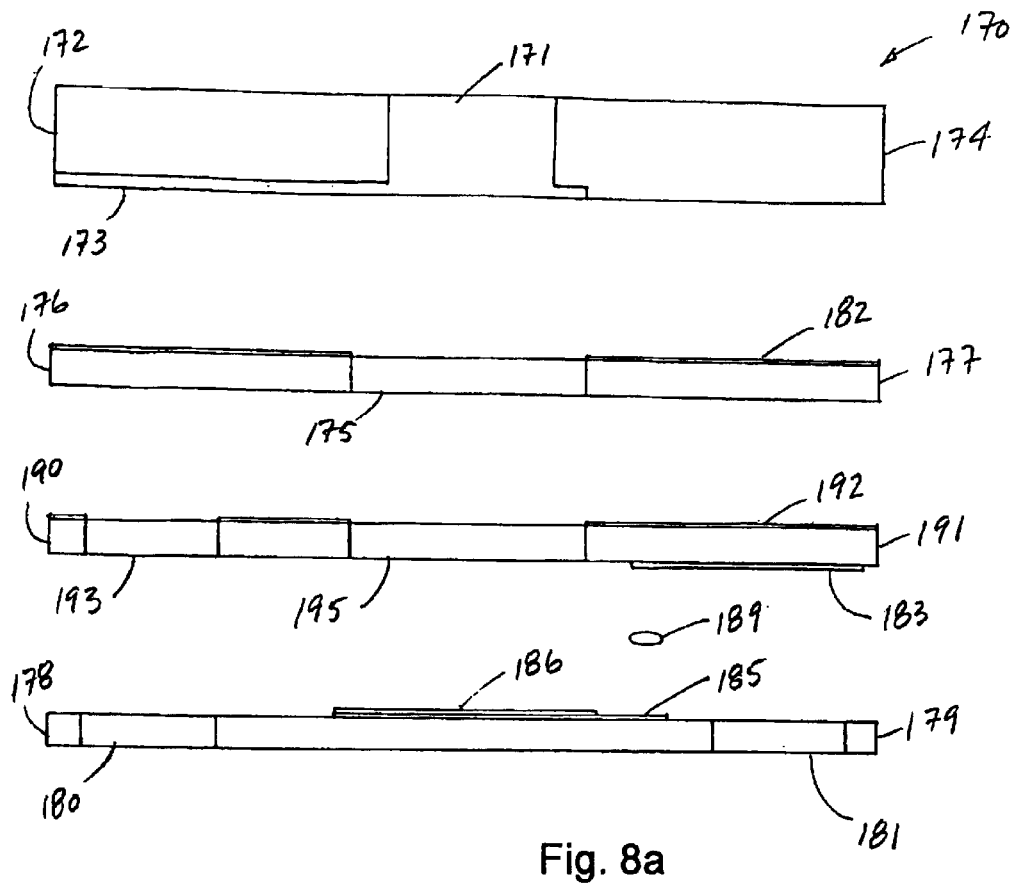
FIGS. 8a, b are diagrammatic sketches as in FIGS. 7a, b showing details of an alternative embodiment of a device according to the invention made using a flexible circuit lamina.
Figure 8B:
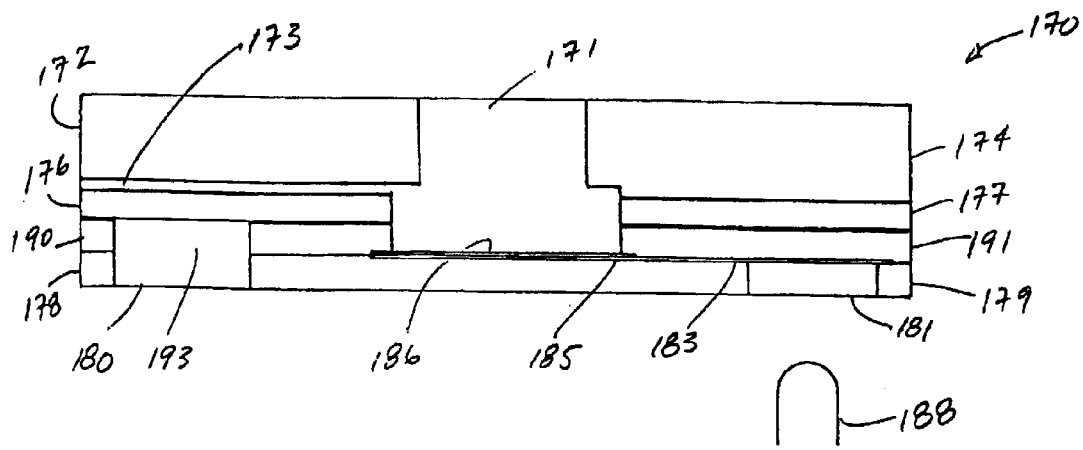

Referring now to FIGS. 8a, 8b, there is shown generally at 170 a portion of an alternative embodiment of a device according to the invention, in transverse section thru a reservoir and microchannel and associated circuitry. The device consists of a base lamina 172, constructed of a generally planar plastic material 174, a seal layer 176, formed of a low fluorescence polymer film 177, a back circuit layer 178, formed of a plastic film 179, and an intermediate circuit layer 190, formed of a polymer film 191 Formed in the polymer base lamina 174 are reservoir 171 and microchannel 173, An opening 175 is formed through the seal layer film 177 in register with the reservoir 171, A front surface of seal layer film 177 is provided with an adhesive 182, which will serve to seal the seal layer and the base layer together when assembled, as shown in FIG. 8b. A back surface of the intermediate circuit layer film 191 is provided with contact conductive trace portion 183 of the circuitry, and a front surface of the intermediate circuit layer film 191 is provided with an adhesive 192, which will serve to seal the intermediate circuit layer film 191 to the seal layer 177 when assembled, as shown in FIG. 8b. An opening 195 is formed through the intermediate circuit layer 190, in register with the opening 175 in the seal layer and with the reservoir 171, An intermediate detection clearance opening 193 is formed through intermediate circuit layer film 191 in register with a detection zone of the microchannel 173, A detection clearance opening 180 is formed through back layer film 179 in register with a detection zone of the microchannel 173, and a contact opening 181 is formed through back layer film 179 in register with the contact conductive trace portion 183, front surface of the back layer film 179 is provided with a second conductive trace 185, having one region in register with a region of the contact conductive trace 183 and another region in contact with a carbon electrode 186, which in turn is in register with the reservoir 171, A conductive adhesive 189 provides for good conductive adhesion between conductive traces 183, 185, when assembled, as shown in FIG. 8b. Referring now to FIG. 8b, an electrical contact 188 in the analytical instrument contacts the contact conductive trace portion of the circuitry by way of the contact opening in the back layer, and a photodetector (not shown in the Figs.) detects the signale in the microchannel through the low fluorescence film of the seal layer by way of the detection opening 180 in the back layer. In this embodiment, the flexible circuit laminate (made up of the two circuit layers) can be constructed separately from the base layer and seal layer, because the seal layer does not include any circuitry. Moreover, because in this embodiment there need not be a good seal between the flexible circuit laminate and the microchannels in the base layer, it is not necesary that the flexible circuit laminate have a surface that conforms precisely with the surface of the base layer.

An embodiment of a microstructure array device according to the invention, provided with flexible circuitry constructed generally as described above, is shown in FIGS. 11a, 11b, 11c. In this example, the elongate flexible film laminate contains a plurality of microstructure arrays arranged serially lengthwise along the laminate. Each microstructure array in this illustrative embodiment includes four microstructures, each configured to carry out an analytic process.

Figures 11A, 11B:
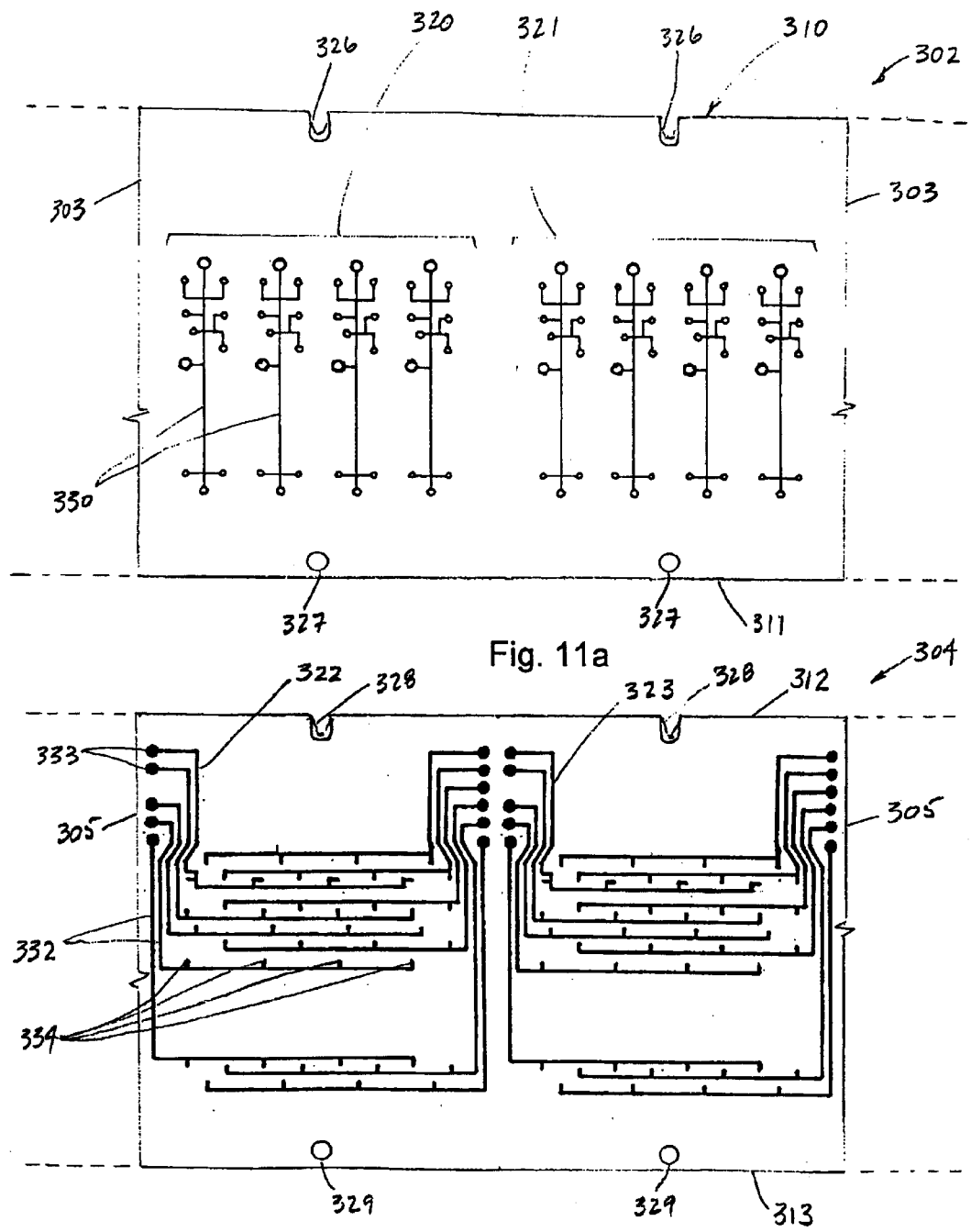

Referring now to FIG. 11a, there is shown a short segment of an elongate flexible film base lamina 302 which extends lengthwise beyond the range of the drawing, as indicated by broken lines extending from the edges 310, 311 of the short segment. The short segment shown, which is limited by lines 303, includes two successive microchannel arrays 320, 321. Each of the microchannel arrays 320, 321 in this illustration contains four microstructures, two of which are indicated for example at 330, each configured and designed for carrying out a receptor binding assay, as described in detail in Example 1 below, with reference to FIG. 9. Near the edge 310 and associated with each array is a pin registration slot 326, and near the edge 311 and associated with each array is a pin registration hole 327.

FIG. 11b shows a corresponding flexible circuit laminate 304, which also extends beyond the range of the drawing, as indicated by broken lines extending from the edges 312, 313, The short segment shown, which is limited by lines 305, includes two circuit layouts 322, 323, each configured to serve a microchannel array 320, 321 (shown in FIG. 11a) in the assembled device. The flexible circuit laminate can be constructed generally as described above with reference to FIGS. 8a, 8b, for example. The circuits consist of conductive traces (two are shown at 332, for example) each connecting a contact terminal (two are shown at 333, for example) to four electrodes (334, for example) each located at a point corresponding to the positions of a reservoir in one of the four microstructures in the array.

Figure 11C:
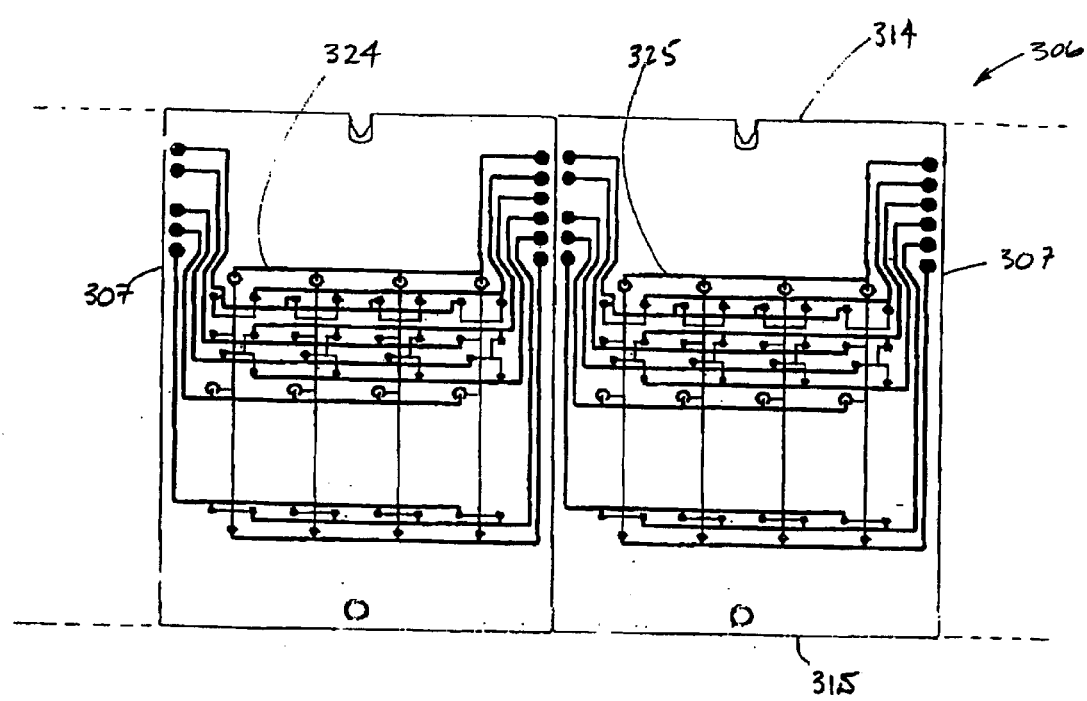

Near the edges 312, 313, the flexible circuit laminate 304 is provided with pin registration slots 328 and holes 329, associated with the circuit layouts such that when the base lamina and the flexible circuit laminate are assembled and the respective slots and holes are aligned, precise superposition of the electrodes over the respective reservoirs is ensured. Referring now to FIG. 11c, there is shown generally at 306 a short segment of an embodiment of an assembled continuous form microstructure device of the invention, made by laminating the base lamina of FIG. 11a and the flexible circuit laminate of FIG. 11b. As in FIGS. 11a, 11b, the device extends beyond the range of the drawing, as indicted by broken lines extending from edges 314, 315; and the short segment shown, which is limited by lines 307, includes two microstructure arrays 324, 325, each capable of carrying out four receptor binding assays under the control of the associated circuit layout.

The laminate is constructed, as described above, so that the contact terminals are accessible by contact points through contact holes in the cover fin Accordingly, as the laminate is carried through the analytical device, sets of contact points are brought into contact with the corresponding sets of contact terminals on the laminate device. The contact points, in turn, are connected to a source of electrical power, which is provided with controls to change the voltages at the electrodes in a pattern determined according to the sequence of electroflow manipulations to be carried out in the microstructures over the course of the assay.

EXAMPLES

Example 1
Receptor Binding Assay

This Example illustrates a microstructure configuration and method for carrying out a membrane-receptor competitive binding assay according to the invention In this Example, cell membrane receptors are attached to solid-phase capture media for facilitating the use of protein receptors in a microfluidic-based assay. Solid-phase attachment of the receptor can be achieved in one of several ways, including, e.g. the use of activated paramagnetic beads or other synthetic particles.

This assay is particularly applicable for receptors belonging to the seven transmembrane family or similar proteins wherein the sequence of amino acids traverses the membrane multiple times. These targets, e.g., the G-protein coupled receptor (or GPCR), are more likely than others to require the physical environment of the membrane lipid bilayer for physiologically relevant interactions. The dopamine receptor is a specific example of the broader class of GPCR proteins.

A membrane-receptor competitive-binding assay in regard to the above is provided. The non-isotopic assay comprises of two binding events. The primary receptor-ligand affinity reaction can be written generally as:

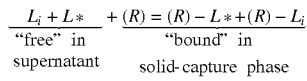

where the library test compound $L_i$ and labeled ligand $L^*$ compete for receptor binding sites (R) on the immobilized cell membrane protein. Once the unbound ligand $L^*$, which remains "free" in the supernatant, is removed, then the bound ligand, which is complexed with the immobilized receptor beads, can be detected using a fluorophore-labeled secondary binding protein. If a biotinylated ligand is employed in the primary bioaffinity reaction, then solid-phase fluorescence detection is possible based on the following binding reaction:

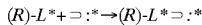

where ⊃:* represents, for example, an avidin-fluorescein conjugate, as the other member of the secondary specific binding pair. Other protocols based on methods of the invention are also possible. For example, a detection scheme may be employed based upon depletion monitoring of the labeled ligand $L^*$.

Figure 9:
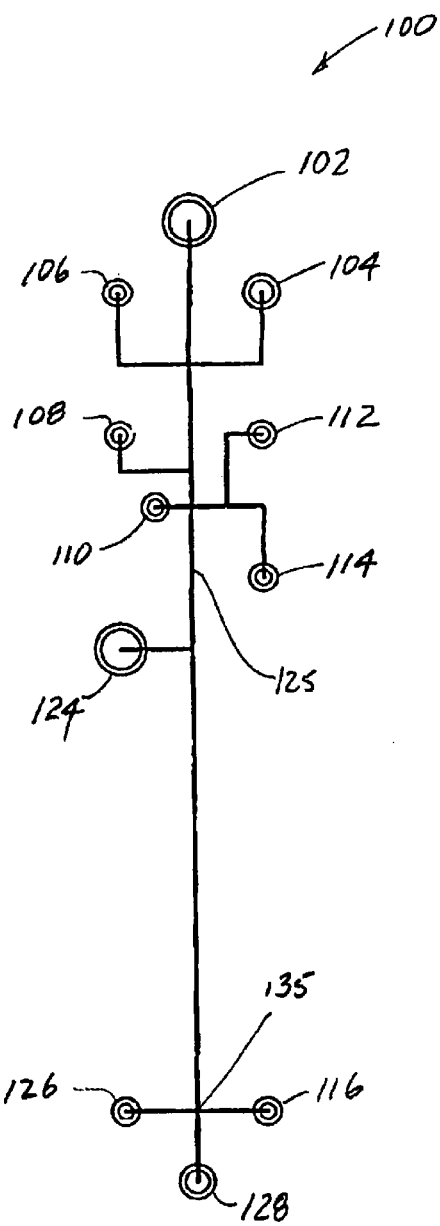
FIG. 9 is a diagrammatic sketch showing a microstructure configuration that can be constructed in a continuous form laminate device of the invention, suitable for carrying out a receptor binding assay.

Such an assay can be carried out using a microfluidic assay device according to the invention, configured, in one embodiment, as shown generally at 100 in FIG. 9. Referring now to FIG. 9, there is shown an assay laminate device 100, on which the microstructure is formed. The microstructure includes chambers and reservoirs that are connected in fluid communication by microchannels. Particularly, card 100 includes a zone 125 in which incubation is carried out and separation and detection can be carried out; a secondary capture and detection zone 135; a number of inlet reservoirs: reservoir 102, which serves as a supply of buffer solution; a reservoir 104, serving as a source of library test compound ligand i; reservoir 106, serving as a source of a biotin-labeled ligand conjugate, or biotinyated tracer; reservoir 108, serving as a source of fluorophore-labeled secondary binding protein, or fluorescent tracer; reservoir 110, serving as a source of bead-immobilized, membrane-bound receptor; wash buffer reservoir 112; reservoir 114, serving as a source of an agent that cleaves the fluorophore tag from the fluorescent tracer conjugate; and capture compound source reservoir 116; and a number of outlet reservoirs: reservoir 124, to receive waste from the binding assay from the fluorescent tracer conjugate; reservoir 126, to receive waste capture compound; and reservoir 128, to receive waste supernatant from binding.

Each reservoir can be provided with an electrode that is connected to a source of electrical power, and potential differences among the various electrodes can be controlled and manipulated to selectively induce electrokinetic transport to and from the reservoirs and within the microchannels and chambers.

In preparation for the assay, the receptors are immobilized as follows. Magnetic latex beads, preactivated to covalently bind protein, are bound to a lectin such as wheat germ agglutinin (WGA). Upon completion of this step, unreacted or exposed bead surface is blocked from nonspecific interactions by incubation with a saturating concentration of carrier protein such as bovine serum albumin or gelatin. Then the WGA coated beads are co-incubated with coil membranes having on them the receptor of interest. This interaction may conclude with an additional blocking step, to remove or inactivate potential sites of nonspecific binding.

With reference again to FIG. 9, the bioanalytical assay proceeds on the microfluidic device 100 as follows.

1. A fixed quantity of receptor-bound beads are introduced into reservoir 110. Then the beads are transferred, by means of an applied magnetic field or electrokinetic flow, to chamber 125 by way of a microchannel in fluid communication with the reservoir and the chamber. In this particular assay protocol, the beads are held in chamber 125 for the duration of the procedure.

2. Next, the compound $L_i$, to be tested for binding ability is moved from reservoir 104 by electrokinetic means through communicating microchannels into chamber 125; and either concurrently therewith or thereafter, a standard compound $L^*$ of known binding properties, is moved from reservoir 106 into chamber 125, This latter compound L* contains a member of a directly or indirectly detectable signal-producing system, for example, covalently attached biotin.

3. After an appropriate series of electrokinetically driven wash steps using wash buffer moved from reservoir 112, a determination is made for the amount of unknown compound $L_i$ that binds by determining the degree to which it displaces the standard compound L*. This is measured by introducing the secondary fluoro-labeled binding protein into reaction chamber 125 from reservoir 108 and allowing the complex of compound and receptor, (R)-L*, to react with the streptavidin which binds biotin with high affinity. The amount of streptavidin captured is monitored directly when a fluorescent label is associated with the streptavidin.

4. In some embodiments of the assay in this Example, the amount of fluorescent label associated with the membranes is determined by direct measurement in the capture zone. In other forms of the assay, the fluorescent label may be attached via a disulfide bond (denoted by ":"). This bond is readily cleaved under reducing conditions. Accordingly, dithiothreitol, or beta mercaptoethanol stored in reservoir 114 may be used to release the fluorescent label (denoted by "*").

5. The fluorescent labeled species can then be separated from other reactants by electrokinetic or hydrodynamic enhanced electroseparation techniques. To facilitate detection, the magnetic beads may be immobilized at a site along the capillary path 125 by application of a magnetic field. The fluorescent label may be detected at that site or at a site 135 downstream therefrom. The fluorescent label may be detected in the fluorescent labeled species, or the fluorescent label may be cleaved and detected separately.

Example 2

Enzyme Assay

This Example illustrates a microstructure configuration and method for carrying out an enzyme assay according to the invention, which can be particularly useful in high-throughput pharmaceutical drug discovery and screening applications.

In this Example, an enzyme, a labeled substrate, and an inhibitor are mixed and allowed to incubate, and then the labeled product of the enzymatic reaction and the labeled unreacted substrate are separated electrophoretically and each is quantitatively determined by detection of the label.

Figure 10:
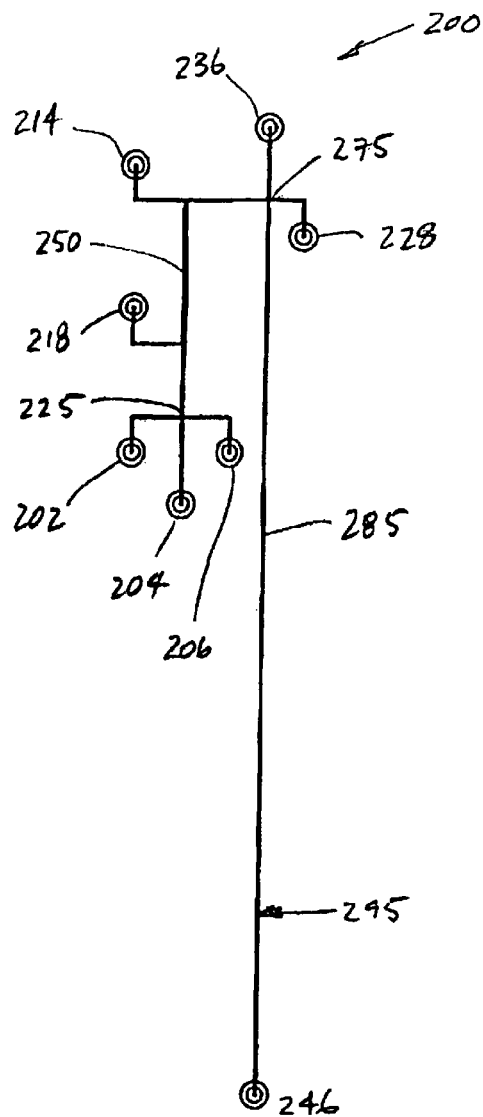
FIG. 10 is a diagrammatic sketch showing a microstructure configuration that can be constructed in a continuous form laminate device of the invention, suitable for carrying out an enzyme assay.

Such an assay can be carried out using a microfluidic assay device according to the invention, configured, in one embodiment, as shown generally at 200 in FIG. 10. Referring now to FIG. 10, there is shown an assay laminate device 200 on which the microstructure is formed. The microstructure includes an incubation chamber 250, an. injection cross 275, an electrophoretic separation channel 285, and detection zone 29S, connected in fluid communication by microchannels with a numbers of reservoirs, including inlet reservoirs: reservoir 202, for supply of enzyme, which is usually a kinase, and containing ATP and $Mg^{2+}$; reservoir 204, for supply of labeled substrate S*, which is usually a fluorophore-labeled peptide reservoir 206, for supply of enzyme inhibitor; reservoir 218, serving as a supply of assay buffer, and employed to electrokinetically transport the product mixture stream to an outlet reservoir 228; and reservoir 236, serving as a supply of running buffer, and employed to electrokinetically transport a metered plug of the product mixture into the separation channel 285 and the outlet reservoir 246; and a number of outlet reservoirs: reservoir 214, to receive a mixture of excess enzyme, substrate, and inhibitor; reservoir 228, for receiving product mixture stream; and reservoir 246, for receiving detection product waste.

Each reservoir can be provided with an electrode that is connected to a source of electrical power, and potential differences among the various electrodes can be controlled and manipulated to selectively induce electrokinetic transport to and from the reservoirs and within the microchannels and chambers.

In some particularly useful embodiments, the enzyme inhibitor is a pharmaceutical drug candidate, and the assay is carried out to determine the effectiveness of the candidate as an inhibitor for the particular enzyme. Usually the enzyme is a tyrosine specific protein kinase such as, for example, Src kinase; and usually the labeled substrate is a fluorophore-labeled peptide such as, for example, cdc-2 peptide.

The enzyme assay proceeds on the microfluidic device 200 as follows.

1. Mixing. Reagents are moved electrokinetically from inlet reservoirs 202 (enzyme), 204 (substrate), and 206 (inhibitor) toward outlet reservoir 214, Mixing of the reagents occurs in mixing cross 225 and in incubation chamber 250.

2. Incubation. The fluid flow is halted electrokinetically by adjustment of the various potentials in order to let enzyme, substrate and inhibitor incubate in incubation chamber 225, 3. Injection. A continuous stream of the product and excess reagent mixture are moved out from the incubation chamber 250 and into the outlet reservoir 228, using the inlet reservoir 218 as the source of the assay buffer to electrokinetically drive the fluid transport.

4. Separation. A plug of the product mixture is electrokinetically injected from the injection cross 275 into the electrophoretic separation channel 285 and then into, waste outlet reservoir 246 using inlet reservoir 236 as the source of the running buffer to electrokinetically drive the fluid transport. As a result of mobility shift produced by conversion of labeled substrate S* to product P*, S* and P* are separated electrophoretically as they are electrokinetically transported in separation channel 285, Laser-induced fluorescence monitoring of the labeled substrate and product is achieved in the detection zone 295, Because the mobility shift is usually expected to result from differences in charge/mass ratio between S* and P*, a gel matrix is usually not required to achieve separation.

As the Examples illustrate, the invention is useful in a wide variety of applications involving techniques and protocols in fields of, for example, cell biology, molecular biology, HLA tissue typing, and microbiology. More specifically, for example, the invention can be applied to techniques for immunodiagnostics, DNA purification from whole blood and other samples, mRNA isolation, solid phase cDNA synthesis, receptor-binding assays, drug screening and discovery, and cell isolation.

Other embodiments are within the following claims. For example, assay devices other than microchannel devices can be adapted in a continuous form assay array format generally as described herein, to provide high throughput systems. For example, the fluids (reagents, samples, etc.) employed in the assay can be mixed and measured in wells (that is, in cavities) constructed in an elongate laminate device, and not necessarily directed by microfluidic manipulation.

And, for example, microstructures or arrays of microstructures may be formed in more than one lamina in the laminated device according to the invention, so that microstructures in one lamina are superimposed over microstructures in another. The superimposed microstructures may, for example, carry out different but related processes or process steps in a fluidic process and, by providing for fluid communication between the laminae, fluids may be transported from one microstructure to another in the course of the process. This permits related processes to be carried out in close proximity under similar conditions, and without a need for transfer of products or byproducts or intermediates from one reaction container (or from one microstructure) to another. Fluid communication between laminae can be provided by, for example, simply perforating the layer that separates the microstructures, and control of the flow through such a perforation can be done, preferably in a valveless fashion, by any of the various means employed for moving fluids within the microstructure of a lamina.

As will be appreciated, although the device according to the invention is described above as being used in continuous processing form, individual microstructures or arrays in an elongate laminate made as described above can be separated one from another, and used as discrete devices in "card" form, each containing a microstructure or an array of microstructures. As may be desired, the elongate laminate may, where such use is contemplated, be made easily separable between successive microstructures or arrays, for example by perforating or scoring the laminate, or cutting the laminate partway through. Use of the laminate in this way preserves the advantages of continuous form in the manufacture of the device, and replaces advantages of using the device in continuous form with advantages of handling discrete card-form microfluidics devices.

Approaches to aligning the laminae during manufacture other than through holes or notches can be used, for example, techniques employing optical, electrical, and ultrasonic alignment, or employing other mechanical means such as ratchets.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A continuous form microstructure array for conducting a plurality of assays, the microstructure array comprising:
    a flexible elongate laminate having a plurality of microstructures arranged therein, the flexible elongate laminate comprising a first lamina having a first surface, a second lamina having a second surface, and a flexible circuit laminate adjacent to the first lamina, wherein at least one of the first or second lamina has a plurality of openings so that whenever the first surface of the first lamina apposes the second surface of the second lamina each opening of the plurality of openings is in fluid communication with one of said plurality of microstructures, and wherein the flexible circuit laminate comprises a plurality of electrodes, each electrode being in contact with an electroflow medium whenever the electroflow medium is supplied to said microstructures, each of said microstructures comprising:
    a sample supply reservoir at an opening;
    a sample drain reservoir connected to the sample supply reservoir by one or more microchannel segments;
    an elution buffer reservoir;
    an analyte waste reservoir; and
    a separation channel connecting the elution buffer reservoir and the analyte waste reservoir and intersecting and being in fluid communication with said one or more microchannel segments; and
    wherein the flexible elongate laminate forms a roll or or an accordion-folded stack.

2. The microstructure array of claim 1 wherein said microstructures of said array are arranged in a 12×8 orthogonal arrangement or in a 24×16 orthogonal arrangement.

3. The microstructure device of claim 2 wherein said first lamina, said second lamina, and said flexible circuit laminate are plastic.

4. A continuous form microstructure array for detecting one or more analytes produced in a plurality of assays, the microstructure array comprising:
    a flexible elongate laminate forming a roll or or an accordion-folded stack, the flexible elongate laminate having an array of microchannel structures arranged therein, the flexible elongate laminate comprising a first lamina having a first surface and a second lamina having a second surface, wherein at least one of the first or second lamina has a plurality of openings so that whenever the first surface of the first lamina apposes the second surface of the second lamina each opening of the plurality of openings is in fluid communication with one of said plurality of microchannel structures, each of said microchannel structures comprising:
    a sample supply reservoir at an opening;
    a sample drain reservoir connected to the sample supply reservoir by one or more microchannel segments;
    an elution buffer reservoir;
    an analyte waste reservoir;
    a separation channel connecting the elution buffer reservoir and the analyte waste reservoir and intersecting and being in fluid communication with said one or more microchannel segments; and
    a plurality of electrodes connected to conductive traces to generate an electric field between the sample supply reservoir and the sample drain reservoir when an electroflow medium is present in the one or more microchannel segments and to generate an electrical field between the elution buffer revervoir and the analyte waste reservoir when an electroflow medium is present in the separation channel.

* * * * *